(12) United States Patent
Nadeau

(10) Patent No.: US 6,363,328 B1
(45) Date of Patent: Mar. 26, 2002

(54) SOFTWARE CONTROLLED MEAT PROBE FOR USE IN DETERMINING MEAT TENDERNESS

(75) Inventor: Steven P. Nadeau, Guelph (CA)

(73) Assignee: Ontario Cattlemen's Association, Guelph (CA)

( * ) Notice: Subject to any disclaimer, the term of this patent is extended or adjusted under 35 U.S.C. 154(b) by 0 days.

(21) Appl. No.: 09/331,921

(22) PCT Filed: Dec. 31, 1997

(86) PCT No.: PCT/CA97/01019

§ 371 Date: Aug. 27, 1999

§ 102(e) Date: Aug. 27, 1999

(87) PCT Pub. No.: WO98/29742

PCT Pub. Date: Jul. 9, 1998

Related U.S. Application Data

(63) Continuation-in-part of application No. 08/775,497, filed on Dec. 31, 1996, now Pat. No. 5,918,190.

(51) Int. Cl.[7] .......................... G01M 3/20; G01N 33/12
(52) U.S. Cl. .......................... 702/27; 702/28; 702/172; 356/445; 33/511
(58) Field of Search .............................. 702/27, 32, 28, 702/172; 706/15, 16, 20, 21, 25, 26; 452/158, 157, 198; 356/445; 33/511

(56) References Cited

U.S. PATENT DOCUMENTS

| | | | | |
|---|---|---|---|---|
| 4,939,574 A | * | 7/1990 | Petersen et al. | 348/89 |
| 5,668,634 A | * | 9/1997 | Newman | 452/157 |
| 5,944,598 A | * | 8/1999 | Tong et al. | 452/158 |

FOREIGN PATENT DOCUMENTS

| | | |
|---|---|---|
| EP | 0 402 877 A1 | 12/1990 |
| WO | 92/21025 A1 | 11/1992 |
| WO | 93/24832 A1 | 12/1993 |
| WO | 95/08962 A1 | 4/1995 |

OTHER PUBLICATIONS

Howard J. Swatland, Objective Measurement of Physical Aspects of Meat Quality, Reciprocal Meat Conference Proceedings, 1989, pp. 65–74, vol. 42, American Meat Science Association.

H. J. Swatland, Analysis of Signals from a UV Fluorescence Probe for Connective Tissue in Beef Carcasses, Computers and Electronics in Agriculture, 1991, pp. 225–234, vol. 6, Elsevier Science Publishers B.V., Amsterdam.

H.J. Swatland, Bidirectional Operation of UV Fluorescence Probe for Beef Carcass Connective Tissues, Computers and Electronics in Agriculture. 1992, pp. 285–300, vol. 7, Elsevier Science Publishers B.V., Amsterdam.

H.J. Swatland, An Anomaly in the Effect of Temperature on Collagen Fluorescence in Beef, Food Research International, 1993, pp. 271–276, vol. 26, Canadian Institute of Food Science and Technology.

(List continued on next page.)

*Primary Examiner*—Marc S. Hoff
*Assistant Examiner*—Hien Vo
(74) *Attorney, Agent, or Firm*—Alston & Bird LLP

(57) ABSTRACT

A data processor used in the overall process of determining meat tenderness which receives, analyses and graphically displays in a dynamic format collected fluorescence emitted by connective tissue as a meat probe passes by such tissue during either insertion or removal of the meat probe from the meat. The data processor also collects and calculates feature variables based on the data collected during the insertion and removal of the meat probe, and through the use of artificial intelligence and artificial neural network processing can be taught to recognize patterns in the meat probe data indicative of tenderness. The data processor also performs an analysis of probe data to make a prediction of meat tenderness.

21 Claims, 19 Drawing Sheets

OTHER PUBLICATIONS

H.J. Swatland, Correction for Base–Line Drifting in Probe Measurements of Connective Tissue in Beef, Food Research International, 1993, pp. 371–374, vol. 26, Canadian Institute of Food Science and Technology.

H.J. Swatland, T. Nielsen and J.R. Andersen, Correlations of Mature Beef Palatability with Optical Probing of Raw Meat, Food Research International, 1995, pp. 403–416, vol. 28, No. 4, Canadian Institute of Food Science and Technology, Great Britain..

H.J. Swatland, E. Gullett, T. Hore and S. Buttenham, An Effect of Connective Tissue on the Taste Panel Tenderness of Commerical Prime Beef Detected with a UV Fiber–optic Probe.

H.J. Swatland, E. Gullett, T. Hore and S. Buttenham, UV Fiber–optic Probe Measurements of Connective Tissue in Beef Correlated with Taste Panel Scores for Chewiness, 1995, pp. 23–30, vol. 28, No. 1, Canadian Institute of Food Science and Technology, Great Britain.

"Correction for base–line drifting in probe measurements of connective tissue in beef", H.J. Swatland, vol. 26, 1993, Canada, pp. 371–374.

"UV fiber–optic probe measurements of connective tissue in beef correctlated with taste panel scores for chewiness"; H.J. Swatland, E. Gullett, T. Hore & S. Buttenham, vol. 28, 1995, Canada, pp. 23–30.

"Analysis of Signals from UV fluorescence probe for connective tissue in beef carcasses", H.J. Swatland, vol. 6, 1991, Amsterdam, NL, pp. 225–234.

* cited by examiner

SOFTWARE CONTROLLED MEAT PROBE FOR USE IN DETERMINING MEAT TENDERNESS

This application is a Continuation-in-Part of Ser. No. 08/775,497, filed on Dec. 31, 1996, now U.S. Pat. No. 5,918,190.

SCOPE OF THE INVENTION

This invention relates to a data processor which may be used in processing signals and displaying information received from a meat probe to carry out objective determinations of meat quality. The data processor of the present invention analyses feature aspects of the probe data for patterns and makes predictions of meat tenderness based upon similarities to previous samples with known measures of meat tenderness. A system which consistently predicts meat quality, particularly in respect of tenderness, would be of significant benefit to the consumer, and as well to the packing house and to the farmer. The data processor works in conjunction with a meat probe which emits radiation to excite connective tissue to fluoresce. The meat probe is designed to pick up and transmit signals relating to fluorescence and position of the probe to the data processor. The data processor then analyses the data required from the meat probe and displays the information in graphical format on a display device.

BACKGROUND OF THE INVENTION

It is well known in the art that connective tissue is a major factor in variation of tenderness between different cuts of meat. Collagen, which is the dominant protein of connective tissue, emits blue-white fluorescence when excited with UV light at around the 370 nm range. There are several different biochemical types of collagen that differ in molecular structure. Of the two dominant types that occur in skeletal muscle and tendons, type I forms large unbranched fibres while type III forms small branched reticular fibres. Hence a meat probe coupled with a data processor capable of stimulating, measuring and analysing fluorescence from a cut of meat can be used in assessing meat tenderness.

The principle of connective tissues in meat fluorescing when exposed to a particular radiation wavelength has been known for some time as described by Swatland, H. J. Objective Measurement of Physical Aspects of Meat Quality, Reciprocal Meat Conference Proceedings, Vol. 42, 1989. Initial investigations in the development of a probe, which is capable of both exciting and collecting fluorescence from connective tissue in meat, are described in Swatland, H. J. Analysis of Signals from a UV Fluorescent Probe for Connective Tissue in Beef Carcasses, Computers and Electronics in Agriculture (6, 1991) 225:218 and Bidirectional Operation of a UV Fluorescent Probe for Beef Carcass Connective Tissues, Computers and Electronics in Agriculture (7, 1992) 105:300, both of Elsevier Science Publishers B. V. Amsterdam. The original probe was an adaptation of a fat depth probe used by the Danish Meat Research Institute in Denmark for measuring the depth of fat on pig carcasses. The original probe was adapted by the use of an optical fibre which was inserted in the device. The fibre was cut at an angle so that the interface optics were asymmetrical. Exciting radiation was supplied in the optic fibre from a 100 watt short arc mercury source directed through a heat absorbing filter, a red attenuation filter and a dichroic mirror. Light peaking at 225 nanometers was directed into the proximal end of the optic fibre with a microscopic objective. Fluorescence from the connective tissues in contact with the optical fibre of the probe was measured through the dichroic mirror at the proximal end of the fibre with a flat response silica detector and a radiometer. The dichroic mirror was used as a chromatic beam splitter to separate the outgoing excitation light at 225 nanometer from the incoming fluorescent emission at a wavelength considerably greater than 225 nanometer. A depth measurement device for measuring the depth to which the probe was plunged into the carcass was provided either by an optical shaft encoder to trigger photometer measurements at set increments through the carcass, or a continuously variable analogue device, such as a potentiometer. The operation of the potentiometer can be affected by temperature.

The positioning of the glass optic fibre in the probe was also suggested, instead of being cut at an angle, of being slightly bent or rounded in conjunction with a plurality of additional thin fibres as described in the article by Swatland, H. J., Bi-directional Operation of a UV Fluorescence Probe for Beef Carcass Connective Tissues Computers and Electronics in Agriculture 7(1992) 105:300. The use of the multiple fibres around the glass optic fibre was to gather additional information in respect of shape of the connective tissue as the probe passed by the connective tissue. Extensive analysis of the collected fluorescence from use of the meat probe is described in several papers by Swatland in Food Research International which include Correction for Baseline Drifting in Probe Measurements of Connective in Beef, Food Research International 26, 1993 371:374; An Anomaly in the Effective Temperature on Collagen Fluorescence in Beef, Food Research International, 26, 1993 271:276 and Correlations of Mature Beef Palatability with Optical Probing of Raw Meat, Food Research International, Vol 10, No. 4, pp 403–446, 1995. Swatland also published with others in Swatland et al., An Effective Connective Tissue on the Taste Panel Tenderness for Commercial Prime Beef Detected with a UV Fibre Optic Probe (cite to be inserted) and UV Fibre Optics Probe Measurements of Connective Tissue in Beef Correlated with Taste Panel Scores for chewieness, Food Research International, Vol 10. No. 1, pp 23–30, 1995.

Data collected from a meat probe plunged in a carcass usually includes at least two parameters: depth of insertion of the probe and level of fluorescence. Once this data has been obtained, it is necessary to process, evaluate and present it in some meaningful manner. By processing feature aspects of the data and recognizing and associating patterns in the data with previous patterns where the measure of tenderness is known, it is possible to predict tenderness of a meat sample. In addition, since data presented in table form can be difficult to comprehend, the typical method of display is to use graphical display with depth of penetration on the x axis and level of fluorescence on the y-axis. When viewing data obtained in this way, the graph forms a number of peaks and valleys of varying height and widths. The data will vary from sample to sample in amplitude and variation of amplitude from different positions on the carcass, as well as from carcass to carcass. It was thought that a comparison of the number of peaks, height of peaks, frequency of peaks and width of peaks for various samples of meat all on the same scale allowed one to assess tenderness by virtue of these characteristics. It was generally understood that a print-out of these characteristics, which shows a relatively smooth line, indicated tender meat. Presenting the above characteristics of the fluorescent data always at the same scale was believed to be more than sufficient in assessing and evaluating the information in establishing tenderness. We have now discovered that changing the scale for the representation of the data provides useful visual information in evaluating meat tenderness. It has been found that, in changing the scale, there is useful information in respect of the number of peaks, height of peaks, frequency of peaks and width of peaks where in the scale which normally accommodated tougher pieces of meat, the representation would in essence be flatline. This is useful in allowing an operator to visually assess the structure of the collagen and tenderness of the meat. In addition, we have also discovered that upon analysis of chosen aspects of the data, and comparing those aspects with information from previous cases where meat tenderness is known, it is possible to predict meat tenderness and to categorise the probed sample into a tenderness classification.

SUMMARY OF THE INVENTION

The invention provides a data processor used in the overall process of determining meat tenderness which receives, analyses and graphically displays in a dynamic format collected fluorescence emitted by connective tissue as the probe passes by such tissue during either insertion or removal of the meat probe from the meat. The data processor of the present invention also collects and calculates feature variables based on the data collected during the insertion and removal of the meat probe, and through an innovative technique using artificial intelligence and artificial neural network processing, makes a prediction of meat tenderness.

According to an aspect of the invention, a method for predicting meat quality of a meat sample by analyzing data representative of a fluorescent signal generated by a meat probe inserted in and withdrawn from said meat sample; said data being in two sets, a first set representative of said fluorescent signal generated by said probe on "way in" during probe insertion and a second set representative of said fluorescent signal generated by said probe on "way out" during probe withdrawal; said method comprising:

i) analyzing said data by use of a trained artificial neural network structure where said analysis is carried out on selected said first set of data, said second set of data or both said first and second sets of data;

ii) developing by way of said trained artificial neural network structure analyzing said selected data, a value representative of level of meat quality; and iii) classifying level of meat quality of said meat sample according to said value.

According to a further aspect of the invention, a method of training artificial intelligence software to predict tenderness of a meat sample from a signal representative of fluorescence generated by a meat probe comprises:

i) calculating one or more fluorescent feature variables of:
   total half peak width;
   average half peak width per unit length;
   total number of peaks;
   fractional smooth length;
   number of peaks per unit length;
   average peak height;
   half peak width;
   total peak width (all peaks); and
   average half peak width;

ii) independently obtaining a measure of meat tenderness of said meat sample;

iii) inputting said feature variables into artificial intelligence software;

iv) inputting said measure of meat tenderness into said artificial intelligence software;

v) teaching said artificial intelligence software to recognize patterns within said feature variables and associate said patterns with said measure of tenderness;

vi) repeating steps i) to v) above until said artificial intelligence software is able to correlate said values with said measure of meat tenderness to a value at least greater than 6.

According to a further aspect of the invention, a method of training neural network software to predict meat tenderness from a signal representative of fluorescence using the components of the signal of:

total half peak width;

average half peak width per unit length; and at least one feature variable selected from the group consisting of:
   total number of peaks number of peaks;
   fractional smooth length;
   number of peaks per unit length;
   average peak height; and
   half peak width.

According to another aspect of the invention, a method of training neural network software to predict meat tenderness from a signal representative of fluorescence using the components of the signal of:

total half peak width;

average half peak width per unit length; and at least one feature variable selected from the group consisting of:
   total number of peaks number of peaks;
   fractional smooth length;
   number of peaks per unit length;
   average peak height; and
   half peak width.

BRIEF DESCRIPTION OF THE DRAWINGS

Preferred embodiments of the invention are described with respect to the drawings, wherein:

FIG. 2 is a side elevation of an apparatus in accordance with one aspect of the invention and FIG. 2A is an end view thereof;

DETAILED DESCRIPTION OF THE PREFERRED EMBODIMENTS

Figure 1:
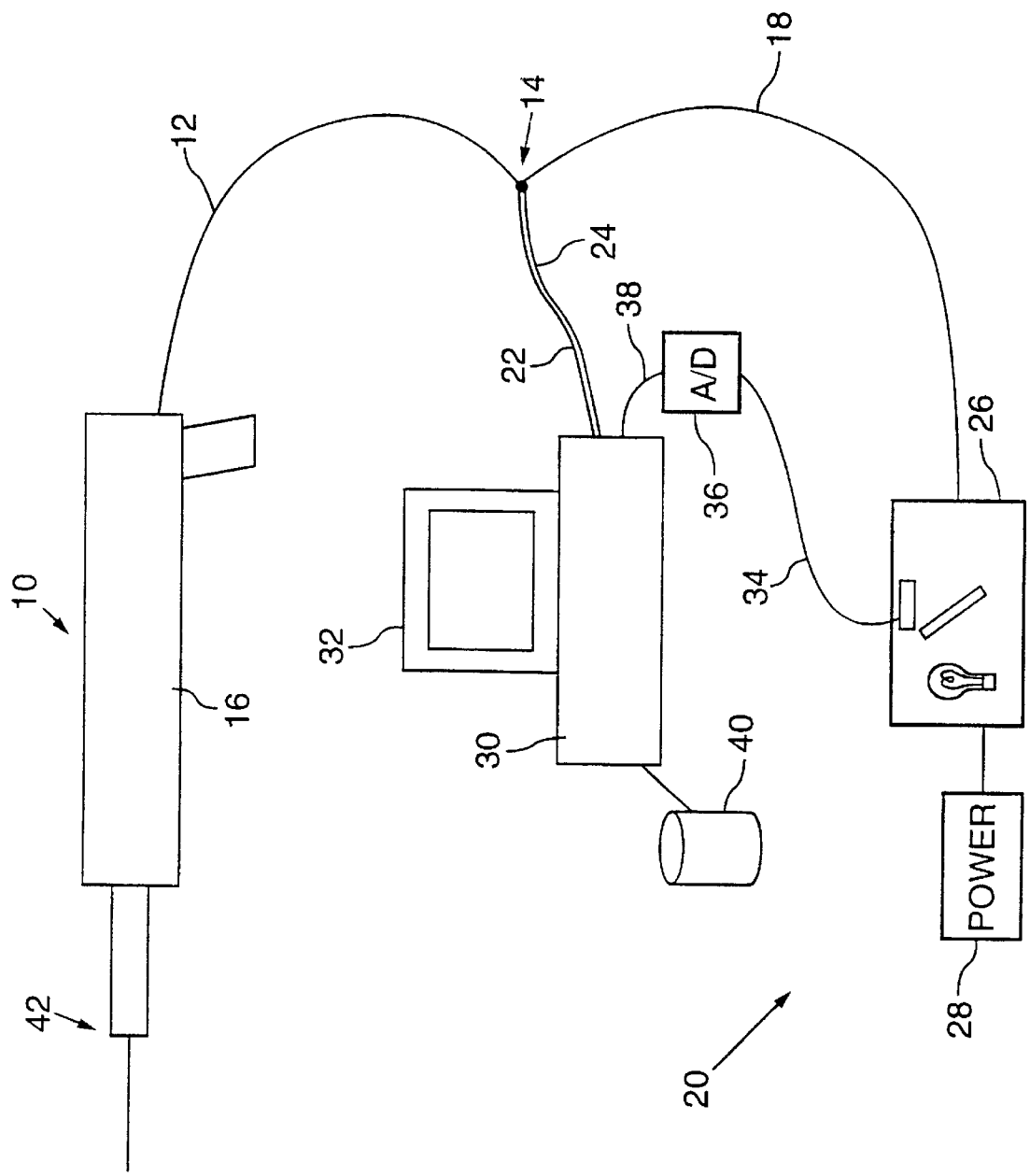
FIG. 1 is a block diagram of the apparatus connected by way of cable to the control and information processing station.

FIG. 1 provides an overview of the meat probe apparatus and the data processor of the present invention. The meat probe apparatus 10 is connected to a controller and information processing station 20 by communications cable 12. The controller and information processing station 20 may be located remote relative to the area where the apparatus 10 is used. Hence the cable 12 is of sufficient length to provide for the remote location of system 20. This permits the location of the system in a controlled area where humidity, moisture, temperature and the like are regulated to ensure proper operation of the system 20. The cable 12, not only carries the optic fibre which transmits exciting radiation and received fluorescent radiation, but as well the electronic cabling which transmits signals between the system 20 and the switches, lights, encoders and the like contained within the main body portion 16 of the apparatus 10, as will be described further with respect to FIG. 2. The cable 12 splits at juncture 14 into the fibre optic cable 18 and the electronic communication cables 22, 24. The fibre optic cable 18 is connected to a light source/fluorescent detector system 26. The light source is powered by the power supply 28. The light source/detector 26 is in communication with the central processor 30 which is coupled to a monitor 32. The light source detector 26 supplies UV radiation in cable 18 which is at the selected wavelength less than 400 nanometers and preferably in the range of 220 to 370 nanometers. This radiation excites collagen to fluoresce as the probe penetrates the meat, where the emitted fluorescence is collected and transmitted through the optic fibre 18 back to the light source/detector 26. The fluorescent intensity is detected and, in turn, transmitted to the central processor 30 through cable 34. The central processor 30 is programmed to record and analyze the collected fluorescence relative to the depth of penetration of the probe to give an indication of the size and number of connective tissues in the meat being penetrated. Correlation and analysis of this fluorescent signal allows one to predict the overall tenderness of the meat section being probed to allow the meat packer, processor or marketer to decide on how that particular portion of meat will be processed or marketed.

Such portions of meat include, for example, the carcass, sides of meat, quarters of meat and the wholesale and retail cuts thereof. It is also appreciated that this technology may also be applied to assessing degree of tenderness of other domestic red meat species, such as lamb, horse, pig, domestic bison, deer, elk and other domesticated ungulates.

The data processing is conducted in two main phases: a data collection phase and a data analysis and display phase. The data analysis and display phase is broken into two parts, a variable computation part where feature variables pertaining to a specific insertion/removal sequence is calculated and a prediction part where patterns in the feature variables are analyzed with reference to previous data sets where the measure of tenderness is known, thereby providing a prediction of tenderness. It is conceivable that both phases may be combined into a real-time system, which would be within the scope of the invention. At the data collection phase of the preferred embodiment, central processing unit 30 is a personal computer capable of running Microsoft Windows Version 3.1, or Microsoft Windows '95 operating system connected to monitor 32 which is capable of graphics display. Computers running other operating systems with a graphical display component, such as Apple Macintosh OS or Unix may also be used. A structured computer programming language environment, which has functions and routines for gathering real-time data from communication ports on the computer, storing data in files, analysing and displaying data in a graphical format could be used for the variable computation part of data analysis phase. In the preferred embodiment, a Pentium™ class computer running DELPHI 2.0 for Windows '95 from Borland International Inc. of U.S.A. is used for programming the data collection variable computation part of the and analysis phase. The programming for the data collection and the feature variable computation part of the data analysis will be explained further in respect of FIGS. 9 to 18. The data analysis programming described in FIGS. 9 to 18 could easily be adapted to other programming languages.

The prediction part of the data analysis phase can be performed on any computer capable of storing or receiving feature variable data sets and running an artificial intelligence program such as neural network software to recognize patterns and make predictions based upon comparison with previously learned patterns for feature variables for which meat tenderness is known. It is appreciated that there are many readily available microprocessors available which runs this type of software an handle the extensive data involved.

Returning to FIG. 1, central processing unit 30 receives probe depth information from apparatus 10 and probe control information through electronic cables 22 and 24 respectively. Cable 34 transmits an analogue fluorescent signal corresponding to emitted fluorescence into analogue to digital converter 36 which converts the fluorescent signal to digital form and then transmitted to central processing unit 30 via cable 38. In the preferred embodiment, said analogue to digital converter 36 operates at a sampling frequency of 50 kilohertz. During the data collection phase, the apparatus 10, sends sampling control information regarding the carcass number, sample number and direction of probe unit (penetration pass or withdrawal pass) to central processing unit 30 via cable 24 while information regarding probe depth of penetration is transmitted via cable 22, as will be described in further detail in FIG. 2. The data processor of the present invention reads control and depth information from cables 22, 24 and fluorescence information from cable 38 and writes the corresponding data values to a raw data file stored on storage disk 40. To initiate data collection, a signal from the apparatus 10 is received through electronic cable 24 to store information regarding the carcass number, sample number, and direction of movement (penetration pass or withdrawal pass) of the meat probe 42. The data processor of the present invention monitors the probe depth signal from electronic cable 22 for changes in probe depth. When a predetermined unit of change in probe depth is detected, the data processor reads the fluorescent signal from input on cable 38. The data processor then stores a carcass number, sample number, probe direction, depth, and fluorescence to storage disk 40. It is important that the data processing unit operates at a sufficient speed to allow all information gathered from cables 22, 24 and 38 to be read and written to the raw data file before the next change in probe depth is detected. Once the probe is fully inserted, a manually triggered change of direction signal is generated at the probe and is received through electronic cable 24 signalling the data processor to change the value for direction of the movement of the probe. In a like manner, the data processor gathers the signals through cables 22, 24 and 38 as the probe is withdrawn and writes such values to data disk 40. When a single penetration and withdrawal is completed, the next carcass signal is transmitted through electronic cable 24 to central processor 30. When the operator of the probe moves on to the next sample position, the operator sends the signal from the control on the apparatus 10 through electronic cable 24 to commence collecting data for the next position on the same carcass. Once sampling is complete for one carcass, the operator, via the controls on the probe, sends the signal, via electronic cable 24, to central processor 30 to commence data collection for a new carcass.

Figure 2:
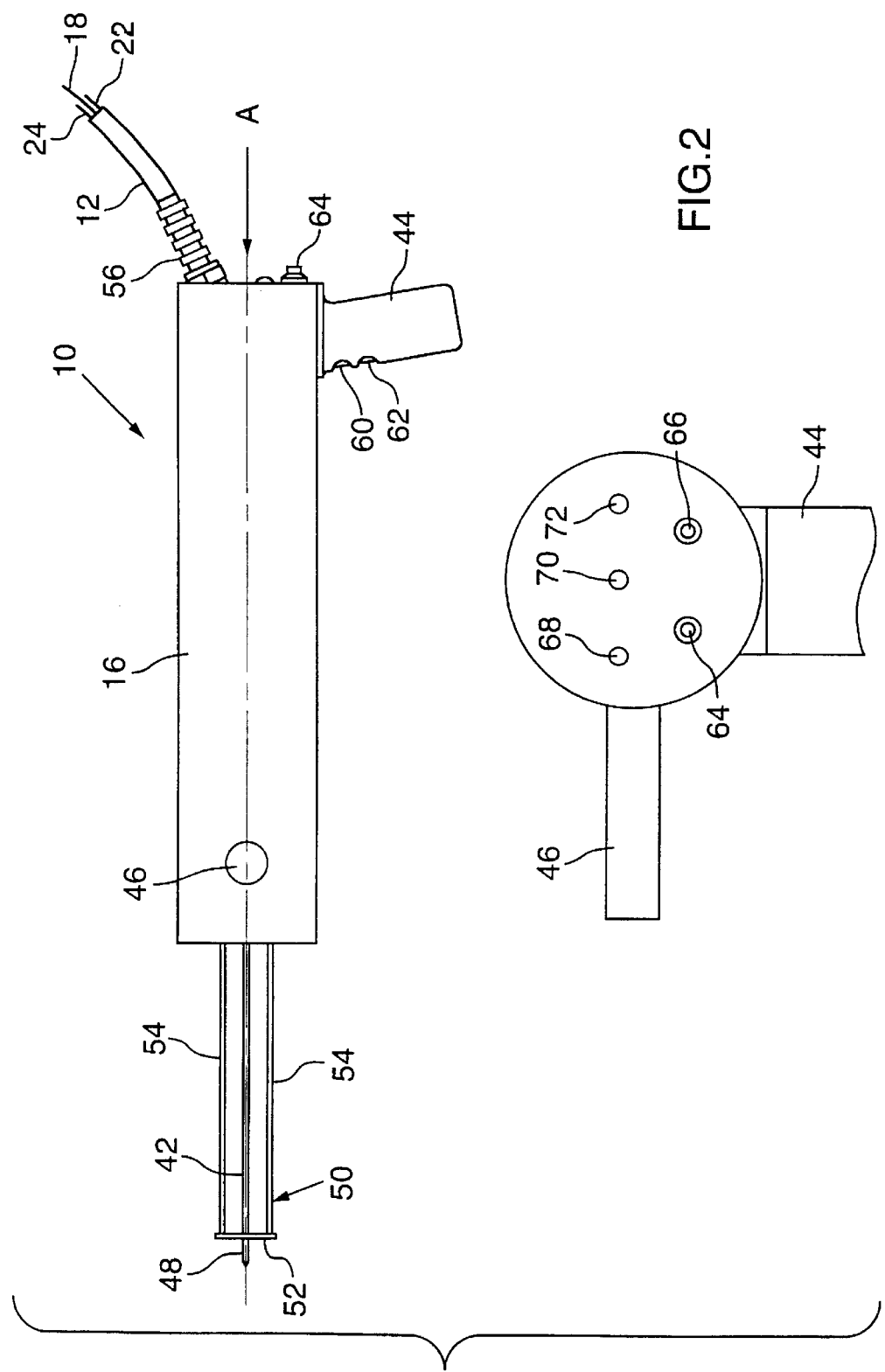

The apparatus which is used in assessing meat tenderness, is shown in FIG. 2. It is understood that the apparatus 10, although shown for use by hand, may also be used in conjunction with robotics. Such robotic use of the apparatus may result in the apparatus having different provisions for carrying out various functions, such as measurement of depth of penetration of the probe and manual activation of various switches on the apparatus 10, however the signals sent to the data processor of the present invention remain the same. The end view of the apparatus 10 is shown in view (A) of FIG. 2.

The advantages and features of this probe are described in applicant's PCT application CA 97/00810 the subject matter of which is hereby incorporated by reference.

In order to facilitate discussion of the software and data analysis, an aspect of the probe is briefly described as follows. The apparatus 10 has a main body portion 16 with a pistol grip 44 and a laterally extending handle 46. The meat probe 42 extends outwardly of the main body 16 and carries at the probe tip distal end 48 a window for the optic fibre as well as a sharp tip for piercing the meat as the probe is plunged into the meat. In order to measure the depth of penetration of the probe tip 48, a plunger 50 has a meat contacting ring 52 which surrounds the probe tip 48. The ring 52 is mounted on rods 54 which extend into the main body 16. Movement of the rods into the main body 16, as will be described with respect to FIG. 4, establishes the depth of penetration of the probe. A connector 56 connects the communications cable 12 which carries the optic fibre 18 as well as other electronic communication cables 22 and 24. The cable 12, not only carries the optic fibre which transmits exciting radiation and receives fluorescent radiation, but as well the electronic cabling which transmits signals between the system 20 and the switches 60, 62, 64 and 66 and lights 68, 70 and 72, as well as encoders and the like contained within the body 16 of the apparatus 10.

The pistol grip 44 for the apparatus 10 has two grip switches 60 and 62 as well as two thumb switches 64 and 66, as shown in view (A) of FIG. 2. Above switches 64 and 66 are three spaced apart lights 68, 70 and 72. During use of the apparatus 10, finger switch 62 may be used to initiate the central processor system, as will be described with respect to FIGS. 9 to 18, to indicate the next test run, or to simply display on the central processor the previously saved test run. Switch 60 may be used to signal the central processor that the penetration of the probe into the meat has stopped and that the next step will be removal of the probe from the meat. Switch 64 may be contacted with the thumb to signal the next carcass to be sampled and switch 66 may be used to indicate in sequence the sampling sites as will be discussed in more detail with respect to FIG. 5. Diode lights 68, 70 and 72, depending on their sequence of on/off modes, indicates to the operator the status of the central processor. For example, with just light 68 in the "on" mode indicates testing may begin. Just light 70 being on indicates that the device is being inserted into the meat and light 72 being on indicates withdrawal from the sample. All lights being "ON" indicates processing of data and not to commence use. Combinations of red and green colours for each light 68, 70 and 72 may be used to signal other conditions, such as warnings, errors, keyboard input required and the like. Switches 64 and 66 greatly facilitate the use of the hand-held apparatus 10 to ensure that the sampling is correlated with the carcass number. The carcasses may be set up on a trolley which begin, for example, with the digit 001 and by sending a signal to the central processor to increment the carcass number, each carcass that comes along can be correlated by the apparatus by simply stepping the switch 64 to the next carcass number. The use of switch 66 is described in more detail with respect to FIG. 5. A further option is that the operator may push both switches 64 and 66 to update the datafile at the remote processing facility.

Figure 3:
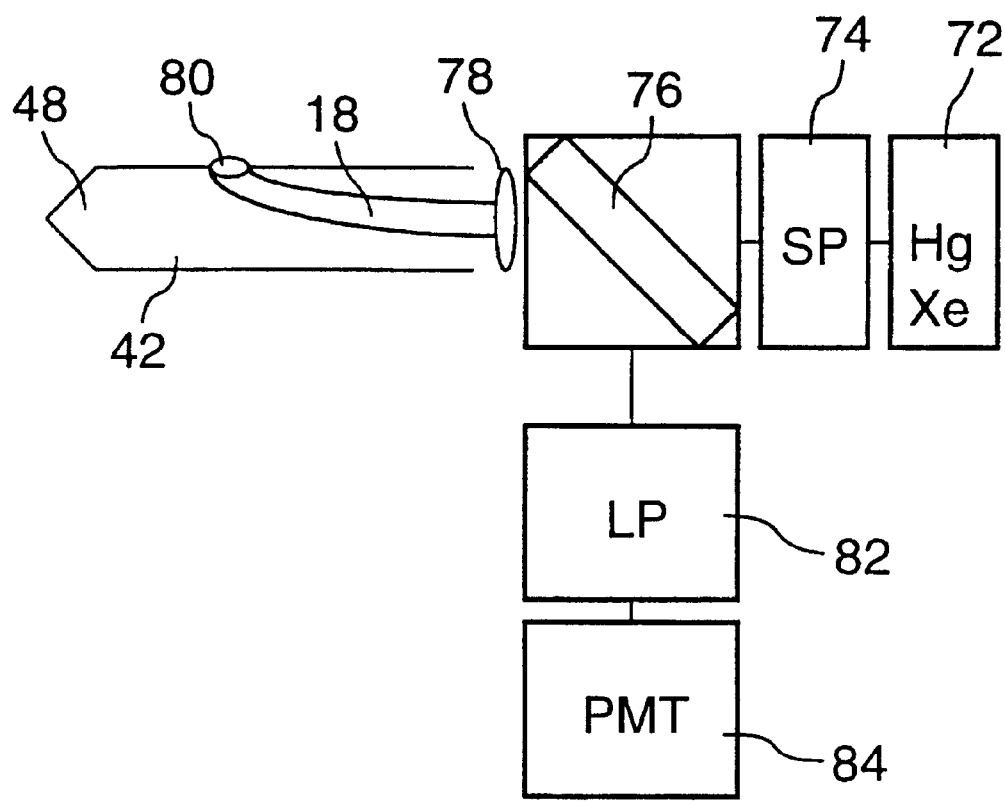
FIG. 3 is a block diagram of the optics power supply, fluorescent detector and probe of the apparatus of FIG. 2.

As shown in FIG. 3, a source of UV light is provided by a mercury-xenon lamp 72. The radiation from the lamp passes through a short pass filter 74 which selects the desired wavelength in the range of 225 nanometers. This filtered light passes through a dichroic mirror 76 which allows the short wavelength radiation at 225 nanometers to pass through to the focusing lens 78 for focusing the UV light into the end of the optic fibre 18. The optic fibre transmits the UV light to the opening or window 80 formed in the side of the probe 42 so as to direct the UV radiation laterally of the probe. Collagen in the vicinity of the opening 80 fluoresces where the emitted fluorescent radiation is collected at opening 80 and transmitted back through the optic fibre 18. In the preferred embodiment, the optic fibre 18 has a protective coating and is preferably made of plastic. Preferred plastic fibres are available from Poly-Optical Products Ltd. of California and General Fibre Optics, Inc. of New Jersey. Such plastic fibres comprise a 1 mm diameter jacketed communications grade plastic fibre. Such fibres are durable, flexible and have low noise to signal ratios. Plastic fibre for these particular wavelengths have been found by us to have superior signal to noise ratio and has greater durability properties compared to optic fibre of glass, such as silica.

The emitted fluorescent radiation passing back through the lens 78 is deflected by the dichroic mirror 76 since the wavelength is greater than a cut-off point, for example, of 400 nanometers. The fluorescence radiation then passes through the long pass filter 82 and the intensity of the florescence is detected by the photometer 84 which may be a standard photomultiplier tube used to detect visible fluorescence. The mercury-xenon light source 72 with short pass filter 74 along with dichroic mirror 76 and long pass filter 82 and photomultiplier tube 84 are encompassed by the block component 26 of FIG. 1. In the preferred embodiment, software is provided in the central processor 30 to analyze the fluorescent signal for both the feature variable computation part and the prediction part of the analysis although each part of the analysis may be performed by a different processor. In the preferred embodiment, in the feature variable computation part, peaks are analyzed from insertion and withdrawal of the probe to allow peak numbers, heights and half-widths to be determined is further discussed with respect to FIGS. 9 to 18. Such information is then processed to correlate the fluorescent signature of the tested section of meat with its anticipated tenderness when consumed in the prediction part of the analysis.

Figure 4:
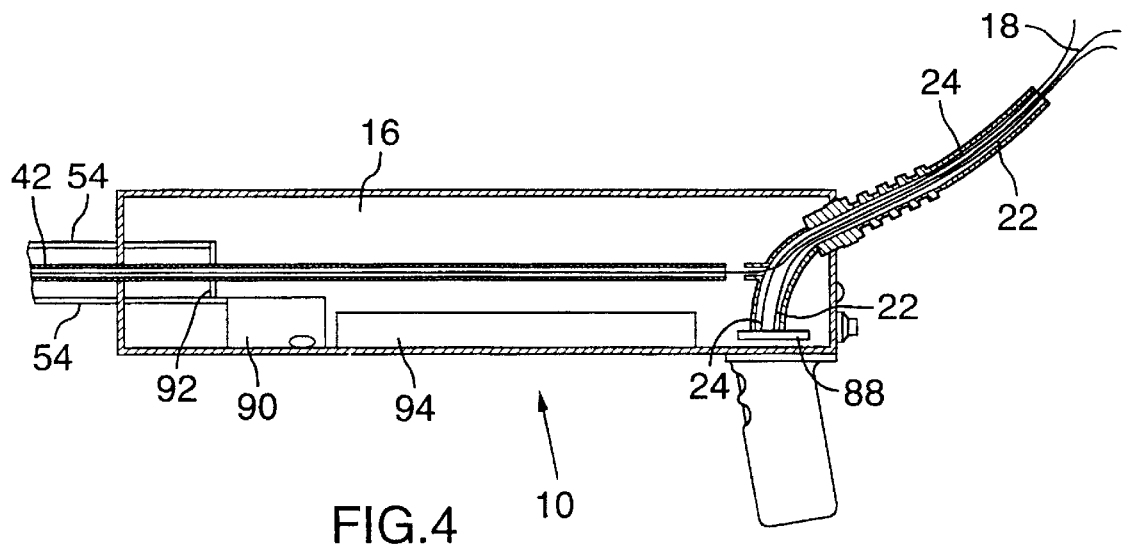
FIG. 4 is a section through the probe of FIG. 2.

As shown in FIG. 4, electronic wires 22 and 24 are fed to a circuit board 88 which directs signals to the switches and lights as described with respect to FIG. 2. Also the circuit board 88 picks up a signal from an encoder 90 which is used to determine at any moment the depth of penetration of the probe tip 48 into the meat. The rods 54 are connected to an end supporting cage 92 which, in turn, is connected to the encoder 90. As the rods 54 recede into the hollow body portion 16, the encoder 90 is moved along an encoded strip 94 to transmit correspondingly the extent to which the tip has moved. The encoded strip 94 may be provided with encoding marks every 50 micrometers so that the exact position of the encoder, as it moves along the strip 94, may be determined by the number of pulses transmitted from the encoder 90 through the circuit board 88 to the central processing unit 30. Such encoding unit, for the predetermined units of depth of penetration, is not temperature sensitive and provides a viable system for correlating the fluorescent peaks with the position of the probe window 80 in the meat.

Figure 5:
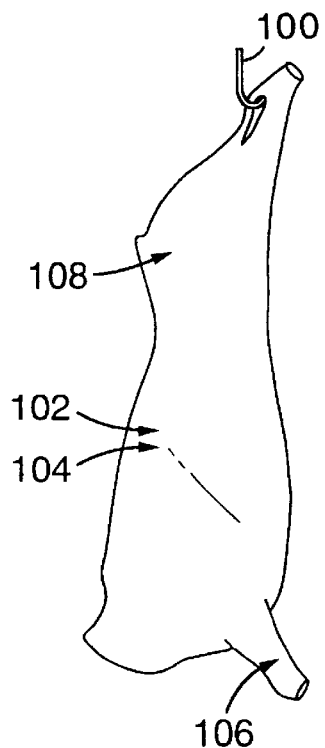
FIG. 5 is a representative side of beef to be probed.

As shown in FIG. 5, a side of beef which may be hung by the hind leg 100 may have four positions for probing meat tenderness; namely, 102, 104, 106 and 108. Before probing the carcass, the thumb switch 64 is indexed to provide the corresponding carcass number and the signal is sent to central processor 30 through electronic cable 24. After each sample test at probe sites 102, 104, 106 and 108, the switch 66 is indexed to send a signal to central processor 30 to increment the carcass number. Hence the fluorescence signature for each position is correlated with the respective carcass. It is appreciated that this same technique may be used to assess tenderness of individual cuts of meat such as single cuts.

Figure 6A:
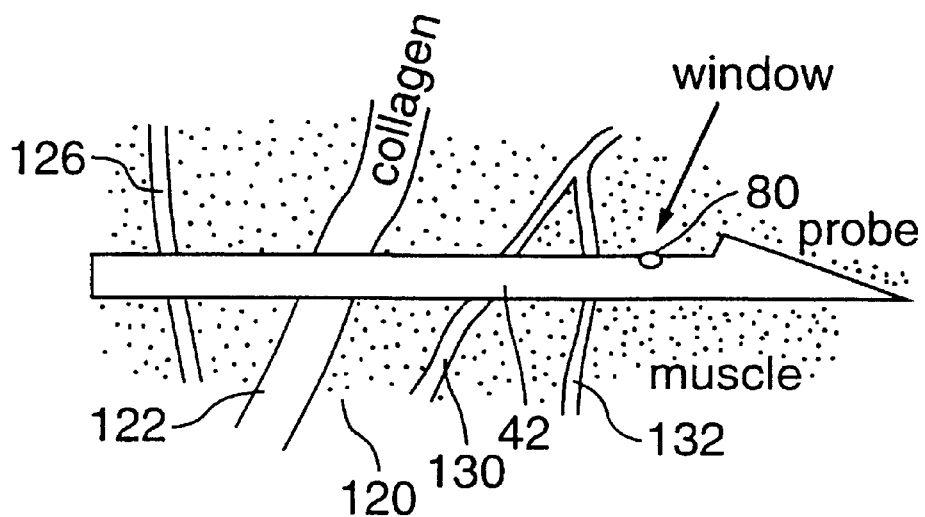
FIG. 6 in (A) shows the probe penetrating meat and in (B) the corresponding fluorescent peaks.
Figure 6B:
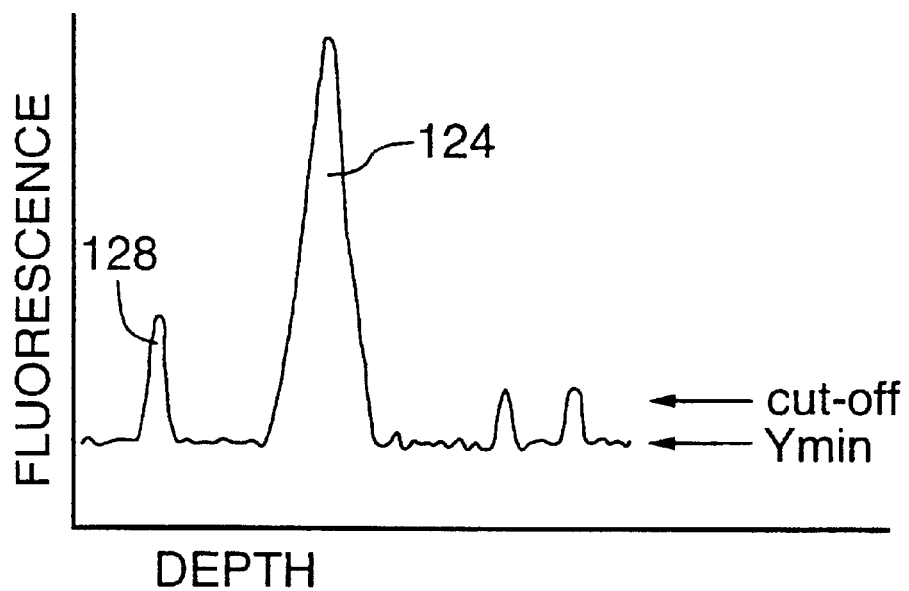

Turning to FIG. 6A, as the probe 42 is inserted through a section of meat 120, the window or end of the optic fibre 80 projects the UV radiation into the meat. As the meat sample is penetrated and, for example, the opening 80 passes through a section of connective tissue in the form of collagen 122, a very significant fluorescent peak is observed at 124 as shown in FIG. 6B. Other peaks may be correlated with minor connective tissue, or cross-linking of meat fibres, such as at 126 where corresponding peak 128 is observed and other small peaks are observed in conjunction with the collagen 130 and 132.

Figure 7A:
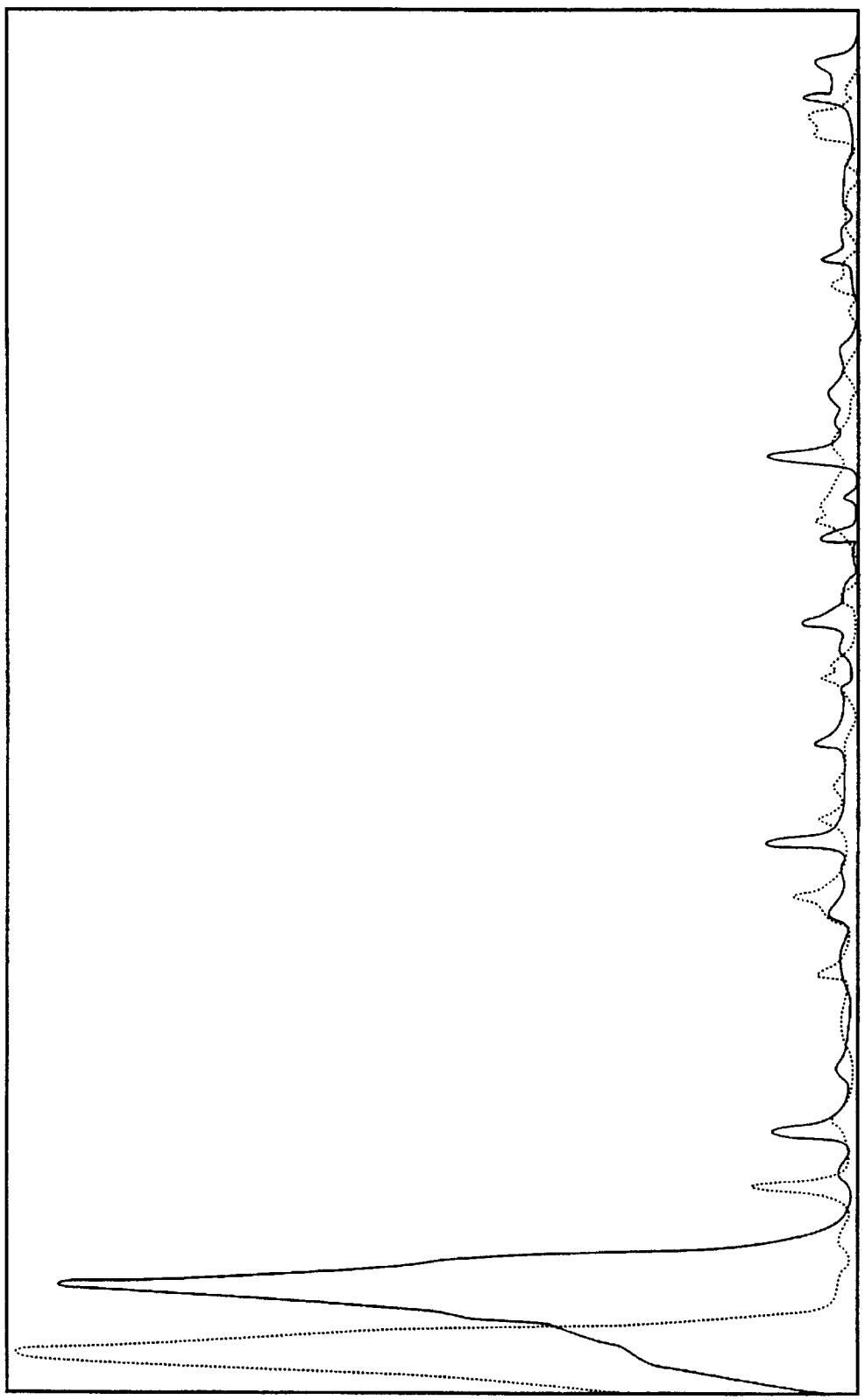
FIG. 7A and 7B are dynamically scaled print-outs of fluorescent peaks associated with probing respectively tender and tough cuts of meat.
Figure 7B:
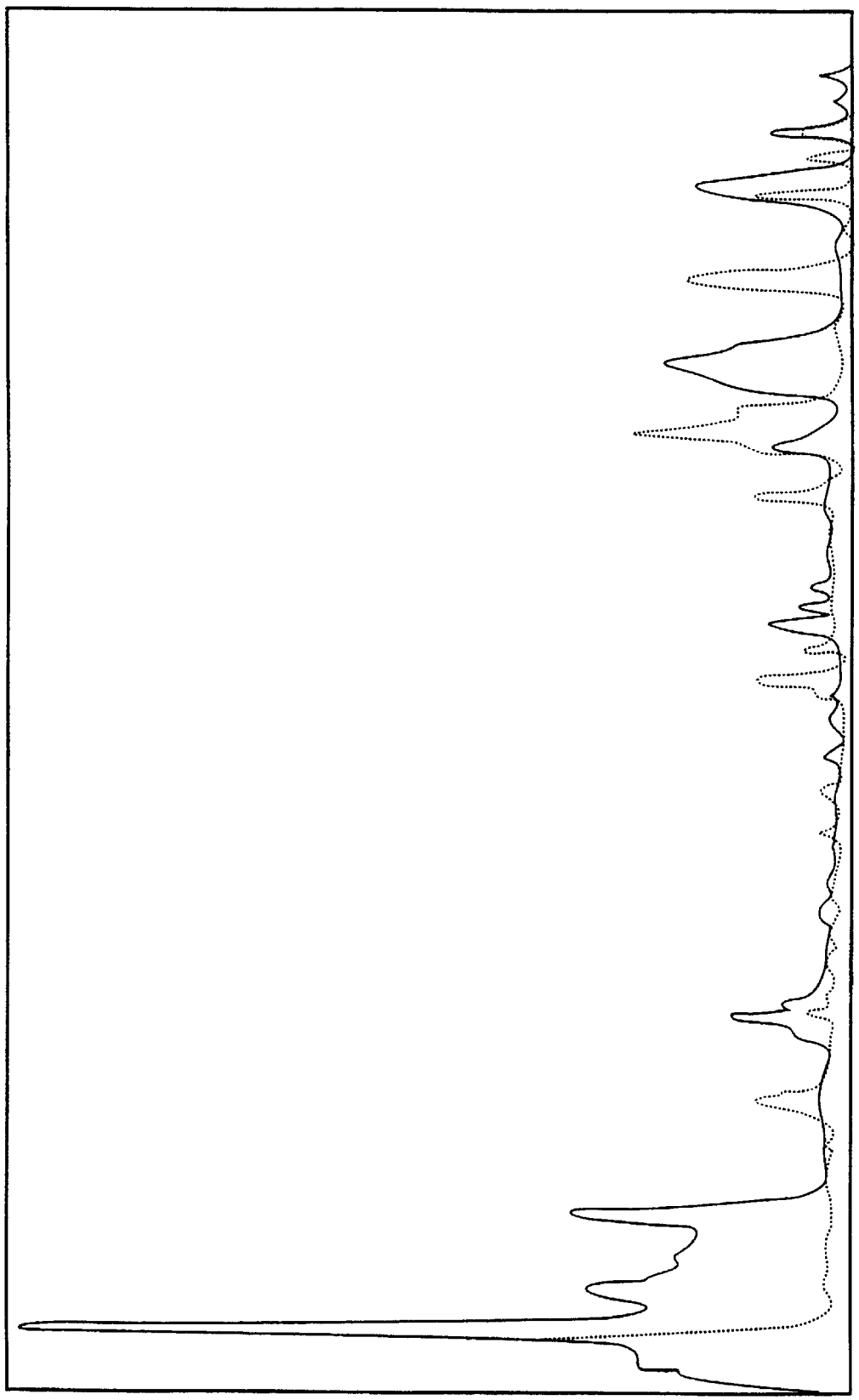

In FIG. 7A and 7B, an exemplary fluorescent read-out with dynamically scaled axes or axis is provided for inserting and withdrawing the probe of FIG. 2. The fluorescent peaks indicate the fluorescence at each indicated depth in the carcass where the width of the peak is indicative of the amount of collagen or other meat entities which are attributed to meat quality, at each depth location. In each of FIGS. 7A and 7B the solid line is representative of the fluorescent radiation received while the probe is penetrating the meat and the dotted line is representative of the fluorescent radiation received while the probe is withdrawn from the meat. Due to compression of the meat fibres the fluorescence on the way out does not match per se with the fluorescence on the way in. There is a slight shift in phase of the peaks but it is apparent that most of the peaks representative of collagen are reproduced on the way out versus the way in. It is important to note that the depth of penetration for each cut of meat is different. The cut of meat of FIG. 7A is loin muscle versus the tougher hip muscle of FIG. 7B. The depth of penetration for the loin muscle was approximately 6 cm whereas the depth of penetration for the hip muscle was approximately 9 cm. The difference in depth of penetration is of course due to the difference in thickness of these two cuts of meat. The intensity scale for FIG. 7A is approximately ⅔ less than the scale for FIG. 7B. The scale for FIG. 7B had to be greater because of the magnitude of the fluorescent peaks being considerably greater in FIG. 7B than 7A. In order to graphically display the respective sets of data while gathering the most information from the data in respect of the tender cut versus the tough cut, the difference in scales were developed in accordance with an aspect of the software of this invention to give the desired graphical representation of the fluorescence in the pre-determined field. It is also understood that the depth of penetration axis may also be dynamically scaled whereby the X-axis is enlarged as much as possible as well.

In FIG. 7A the first peak at the left-hand side is representative of the probe penetrating what is commonly referred to as the "silver skin" around the outer portion of the muscle. Once this outer thick layer of collagen is penetrated the rest of the meat is very tender as represented by the low intensity of the fluorescent peaks and the narrow peak width. Conversely, in FIG. 7B the first peak at the left-hand side of the representation is the silver skin which appears to be thicker than the silver skin of the tender piece of meat and then with continued penetration there are several fluorescent peaks of significant intensity and larger peak width which represents considerably more collagen in the meat and which contributes significantly to the toughness of the meat. Considering the difference in scales of the two representations there is considerably more collagen and thicker collagen in the tougher piece of meat than there is in the tender piece of meat of FIG. 7A.

By virtue of dynamically scaling the data for representation, one skilled in the art can inspect the view of FIG. 7A and FIG. 7B and immediately gather from the representation the relative quality of the two cuts of meat in terms of tenderness.

DATA ANALYSIS OVERVIEW

Figure 8A:
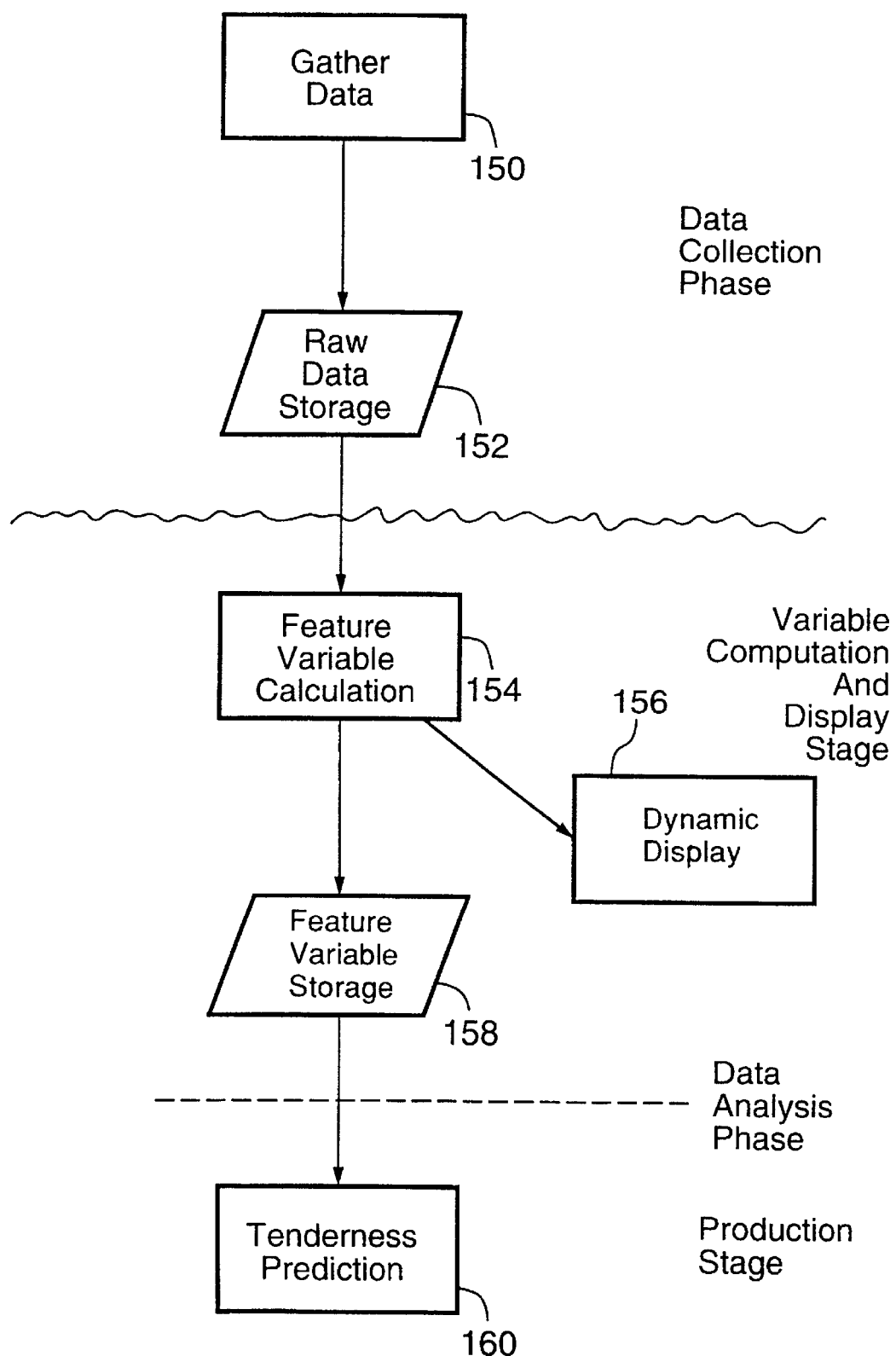
FIG. 8A is a flowchart diagram of the analysis phases of the present invention.

Turning to FIG. 8A, an overview of the phases of processing of data in accordance with various aspects of the present invention is shown. Such data analysis may in essence, in accordance with an embodiment of the invention, implement by data processing what one would do by making a visual comparison of the dynamically scaled representations. The processing is conducted in two phases: a data collection phase, and a data analysis phase. The data analysis phase is conducted in two stages, a variable computation and display stage and a predication stage. At step 150, raw data regarding fluorescence on the insertion and removal of the probe from a meat sample is gathered as previously described with respect to FIGS. 1 to 6B above. At step 152, this raw data is stored on a data storage device. At step 154, the raw data stored in step 152 is retrieved and used in the extraction, calculation of certain features of the raw data, yielding a set of computed feature variables that form a signature particular to the probed meat sample as described with respect to FIGS. 8B to 17 below. At step 156, the fluorescent signal feature variables can be dynamically displayed on a display device as described with respect to FIG. 18. At step 158, the computed feature variables are stored on a data storage device. At step 160, the feature variables stored at step 158 are retrieved and are used in the prediction of tenderness of the probed sample of meat as described in further detail below.

DATA ANALYSIS—VARIABLE COMPUTATION AND DISPLAY

Certain features of the data collection are of special interest in the analysis of fluorescence in connection with meat tenderness. Measurements on both the penetration pass and the withdrawal pass are analysed separately as the level of fluorescence recorded may be different. In some circumstances, the speed at which the probe penetrates the meat may vary on the penetration pass in comparison to the withdrawal pass due to both the difficulty in maintaining a constant velocity when manually inserting the probe and to a compression effect when penetrating the meat. In addition, it is also known that meat and collagen may exhibit a dampening or quenching effect in emitted fluorescence on continued stimulation.

In a preferred embodiment, signal features from the probe which are analysed for the purpose of predicting meat tenderness are: total half peak width, total number of peaks, number of peaks per unit length, average peak height, average half-peak width, average half peak width per unit length, fractional smooth length, total peak width (all peaks) and average half peak width. The analysis of these features of the signal leads to the computation of a set of feature variables which form a signature relating to a specific insertion/withdrawal sequence on a piece of meat. These feature variables, which form a type of signature, are then analysed for patterns by comparison with previously known patterns where tenderness has been measured. This allows a prediction of tenderness to be made. As signal noise may bias the measurements, it is useful to determine these signal features with respect to a threshold level which is slightly above the level of minimum fluorescence.

Of particular interest for display purposes is the identification and analysis of peaks of fluorescence, both with respect to the intensity or height of such peaks as well as the frequency of such peaks. The ease with which such identification is made is facilitated by the dynamic scaling of the information in presentation. By the dynamic scaling of the information in a graphical format, the location and intensity of peaks becomes readily apparent as compared to circumstances when the scale of the axis selected does not allow subtle aspects to be easily identified. With inappropriately scaled axis, small subtle changes in fluorescence which are important indicators of meat tenderness, are lost due to the aggregation of data on a large scale.

For the analysis of the information gathered during the data collection phase, eight separate and different data sets are created from the raw data as follows:

a) way in raw—analysis of the fluorescence on a penetration pass without any correction for spurious data;

b) way in threshold—analysis of the fluorescence on the penetration pass where data analysed is above a set threshold level;

c) way in silver skin—analysis of the fluorescence on a penetration pass only with respect to silver skin;

d) way in silver skin threshold—analysis of the fluorescence on a penetration pass where data relating to the silver skin is analysed at a level of fluorescence above threshold;

e) way out raw—analysis of the fluorescence on a withdrawal pass without any correction for spurious data;

f) way out threshold—analysis of the fluorescence on a withdrawal pass where fluorescence is above the set threshold level;

g) way out silver skin—analysis of the fluorescence only with respect to silver skin on a withdrawal pass; and h) way out silver skin threshold—analysis of the fluorescence on a withdrawal pass with respect to silver skin where fluorescence is above a set threshold level.

The data set creation and the analysis pertaining to the computation of features variables proceeds in three stages: reading of the input files; analysis, calculation and display of data; and writing output files. FIG. 8 is an overview of the data analysis for the computation of feature variables. The values of the variables, in addition to being capable of being displayed, are computed and used in the predication module for determining meat tenderness.

Each insertion/removal pass yields eight different data sets. The analysis particular to each of the eight different data sets for the variable computation part is described in FIGS. 9 to 16. Each of the eight data sets shares common calculations, which are described in FIG. 17.

Figure 8B:
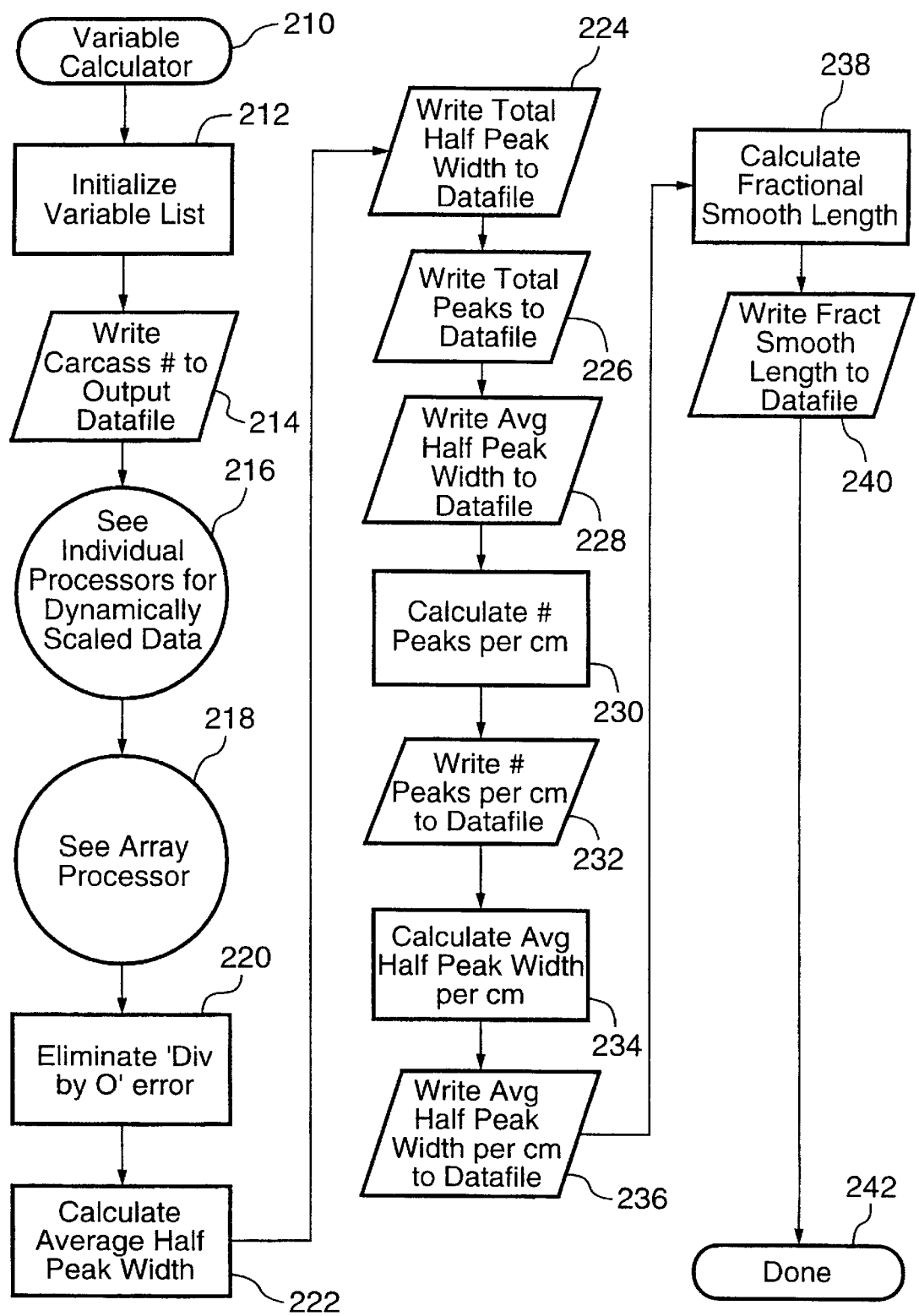
FIG. 8B is a flowchart diagram of the data analysis and variable calculation aspect of the present invention.

Turning to FIG. 8B, an overview of the feature variable computation part of the data analysis is illustrated. At step 210, the analysis of data is commenced. At step 212, the variables of: a) average half peak width, total peaks, peaks per centimeter, average half peak width per centimeter, and fractional smooth length are initialized. At step 214, the carcass number is written to the output data file which is a flat ACSII text file. At step 216, the dynamically scaled data is processed and displayed, as will be described further in reference to FIG. 18. It is at this stage that the raw data file is opened and the data read into an array for use and processing for each data set. Each data set may utilize its own data set array created from the raw data read in at this step. At step 218, the eight separate groups of calculations for each data set are preformed as described further in reference to FIGS. 9 to 17. At step 220, error correction is provided where the possibility of division by zero in the subsequent calculations is addressed by removing data points where the level of fluorescence is zero from the calculations. At step 222, the average half peak width is calculated from the results of the analysis of half peaks as will be described further with respect to FIG. 17. At step 224, the total half peak width is written to the data file. At step 226, the total number of peaks is written to the data file. At step 228, the average half peak width is written to the data file. At step 230, the number of peaks per centimeter is calculated by the formula: total number of peaks÷total number of centimeters probed. At step 232, the number of peaks per centimeter is written to the data file. At step 234, the average half peak width per centimeter is calculated by the formula: average half peak width÷total number of centimeters. At step 236, the average results of the calculation at step 234 is written to the data file. At step 238, the fractional smooth length is calculated. At step 240, the fractional smooth length is written to the data file. With the completion of step 242, the analysis is complete and the output data file is closed. The output data file therefore contains the values of the feature variables calculated for the eight data sets for a particular insertion/removal pass.

Figure 9:
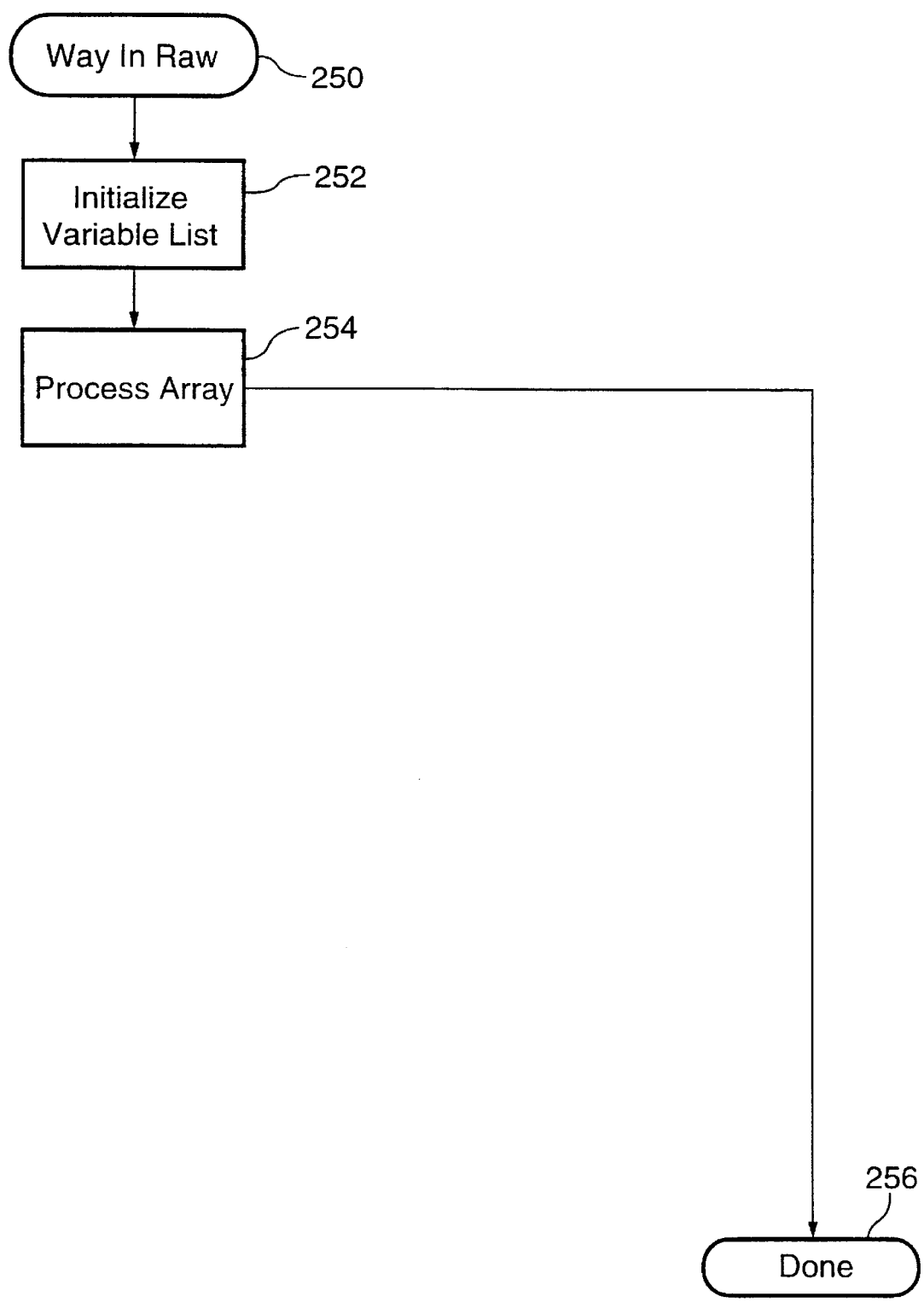
FIG. 9 is a flowchart diagram of the data analysis of raw data of fluorescence on a penetration pass.

Turning to FIG. 9, the analysis of raw data regarding fluorescence on a penetration pass is described in further detail. At step 250, the processing of the data for this data set is commenced by being passed a copy of the raw data array. At step 252, the set of variables with respect to this data set is initialized. These variables for the data set are;

| | |
|---|---|
| startval | represents a data point for depth of penetration; |
| flagup | a logical variable indicating that the level of fluorescence measured at the current data point is greater than the level of fluorescence at the previous data point; |
| flagdown | logical variable indicating that the level of fluorescence measured at the current data point is less then the level of fluorescence at the previous data point; |
| peakcounter | the number of peaks in this data set; |
| peakval | the position of penetration at which the peak occurs; and |
| total halfpeak width | the sum of all half peak widths for the this data set. |

Figure 17:
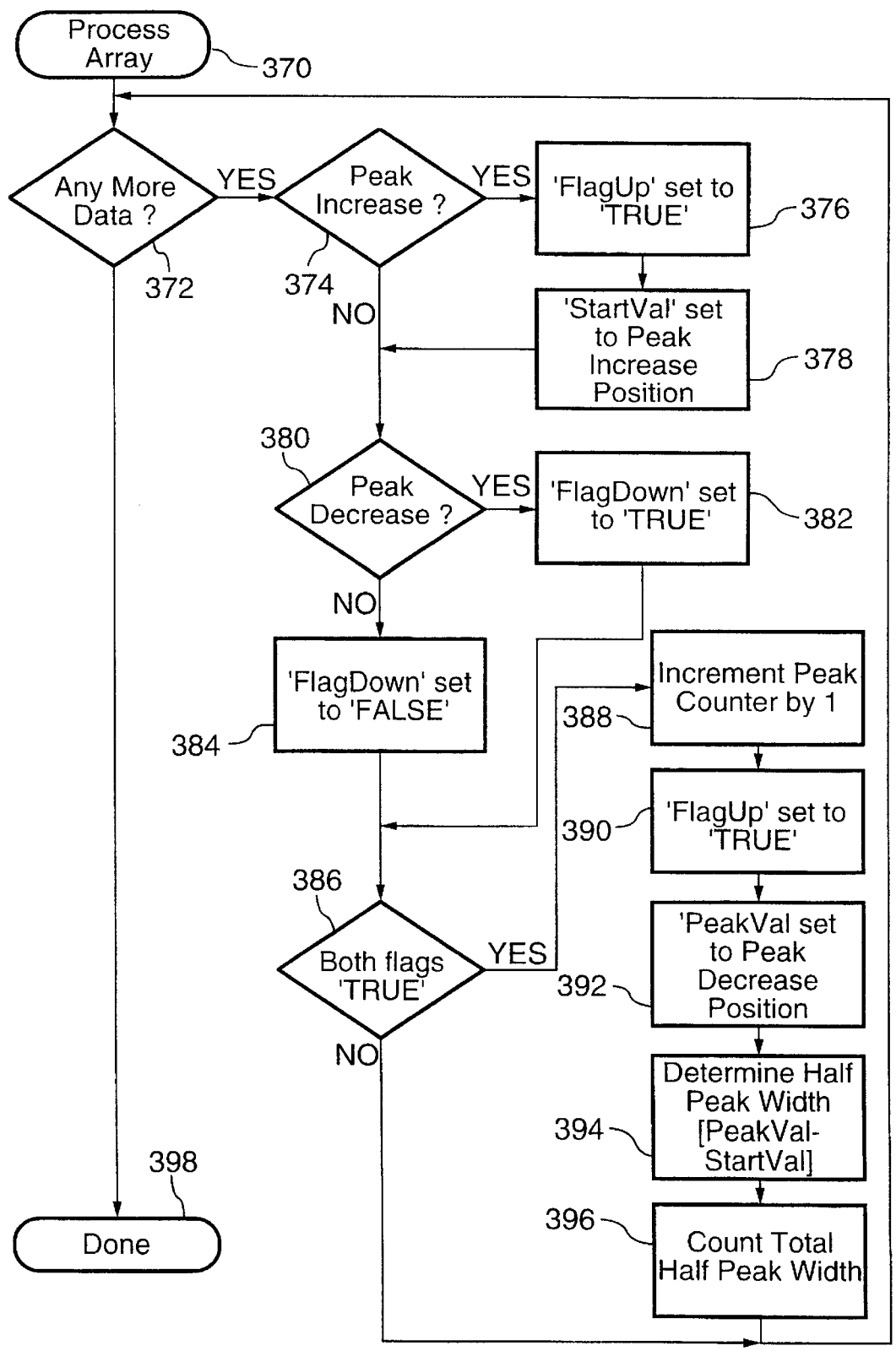
FIG. 17 is a flowchart diagram of the data analysis for peak and half-peak levels of fluorescence.

At step 254, the variables from step 252, and a copy of the raw data array is passed to the analysis routine as is further described with respect to FIG. 17. At step 256, the analysis for this data set is complete and the procedure terminates.

Figure 10:
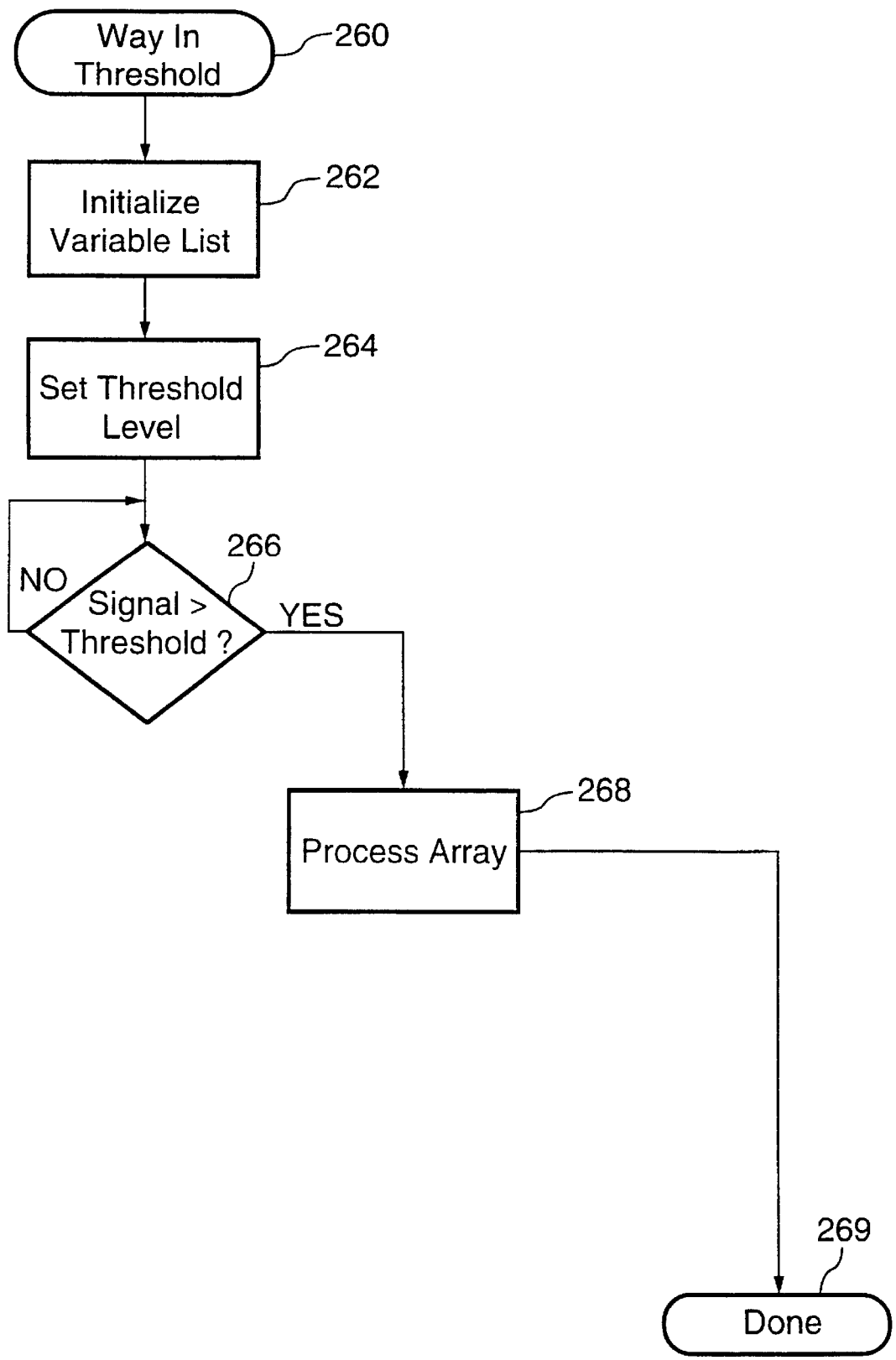
FIG. 10 is a flowchart diagram of the data analysis of fluorescence which is above a threshold level on a penetration pass.

Turning to FIG. 10, the data analysis for fluorescence which is above a threshold level on a penetration pass is described in further detail. At step 260, the data analysis for this data set commences by being passed a copy of the raw data array. At step 262, the variables for the data set analysis are initialized. These variables are the same as the variables described with respect to FIG. 9 except that there are instances particular to this data set. At step 264, the threshold level is set in accordance with the minimum fluorescence times the threshold value. The threshold value is equal to 1.05 for 5% and 1.1 for 10% threshold.

At step 266, the data is screened to obtain a subset of data which represents values above the threshold level. Each data point in the raw data array on the penetration pass is analysed to determine whether the level of fluorescence is above the threshold. The subset of data, in array format meeting the criteria of step 266, as well as the initialized variables at step 262 are passed on to be processed as indicated at step 268. The processing of step 268 is described in further detail with respect to FIG. 17. Once the processing is complete, the procedure terminates as indicated at step 269.

Figure 11:
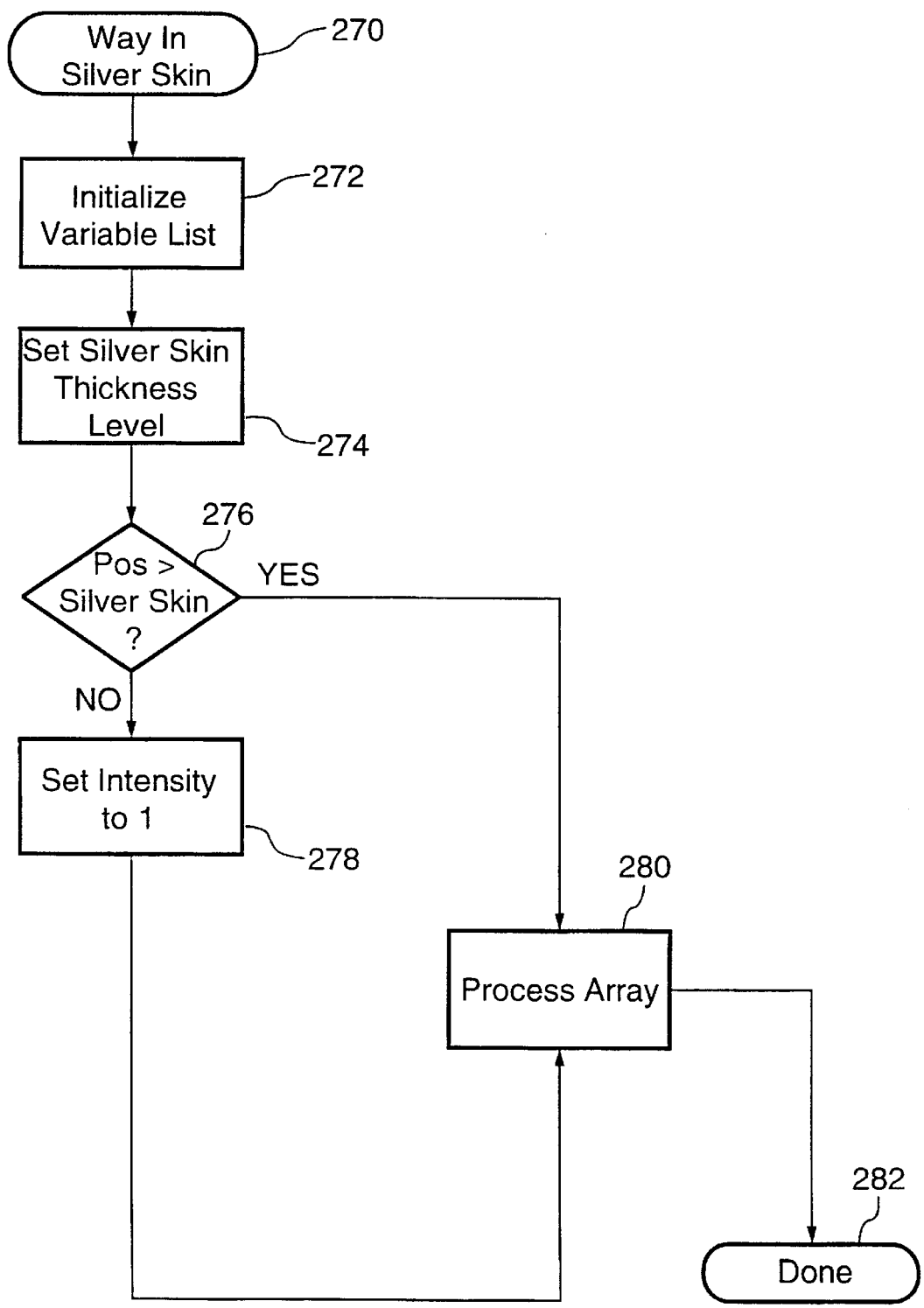
FIG. 11 is a flowchart diagram of the data analysis of fluorescence of silver skin on a penetration pass.

Turning to FIG. 11, the data analysis with respect to fluorescence of silver skin on a penetration pass is described in further detail. At step 270, the processing for this data set is commenced by being passed a copy of the raw data array. At step 272, the variables for this data set are intialized. These variables are the same as the variables described with respect to FIG. 9 except that there are instances particular to this data set. At step 274, the silver skin thickness level position in the meat sample is set. This may be accomplished by counting the number of increments from the Mylar® encoded strip where 200 counts is equivalent to 1 cm in thickness, as described in the aforementioned application CA07/00810. At step 276, preprocessing of the passed raw data array is provided. For each data point in the array corresponding to a penetration pass, the position of penetration is compared with the position of silver skin in the meat sample. If the penetration position is not greater than the silver skin position, the level of intensity of fluorescence for that point in the data set is set to 1 as indicated at step 278. The data point is then passed on to be processed as indicated at step 280. However, if the position of penetration for the data point is greater than the silver skin position set at step 274, the level of intensity of fluorescence is not adjusted and the data point is passed on to be processed at step 280. The variables which were initialized at step 270 as well as the appropriate data points in array format from steps 276 and 278 are passed on to be processed at step 280 as is described in further detail with respect to FIG. 17. Once the data processing is complete for this data set, this procedure terminates as indicated at step 282.

Figure 12:
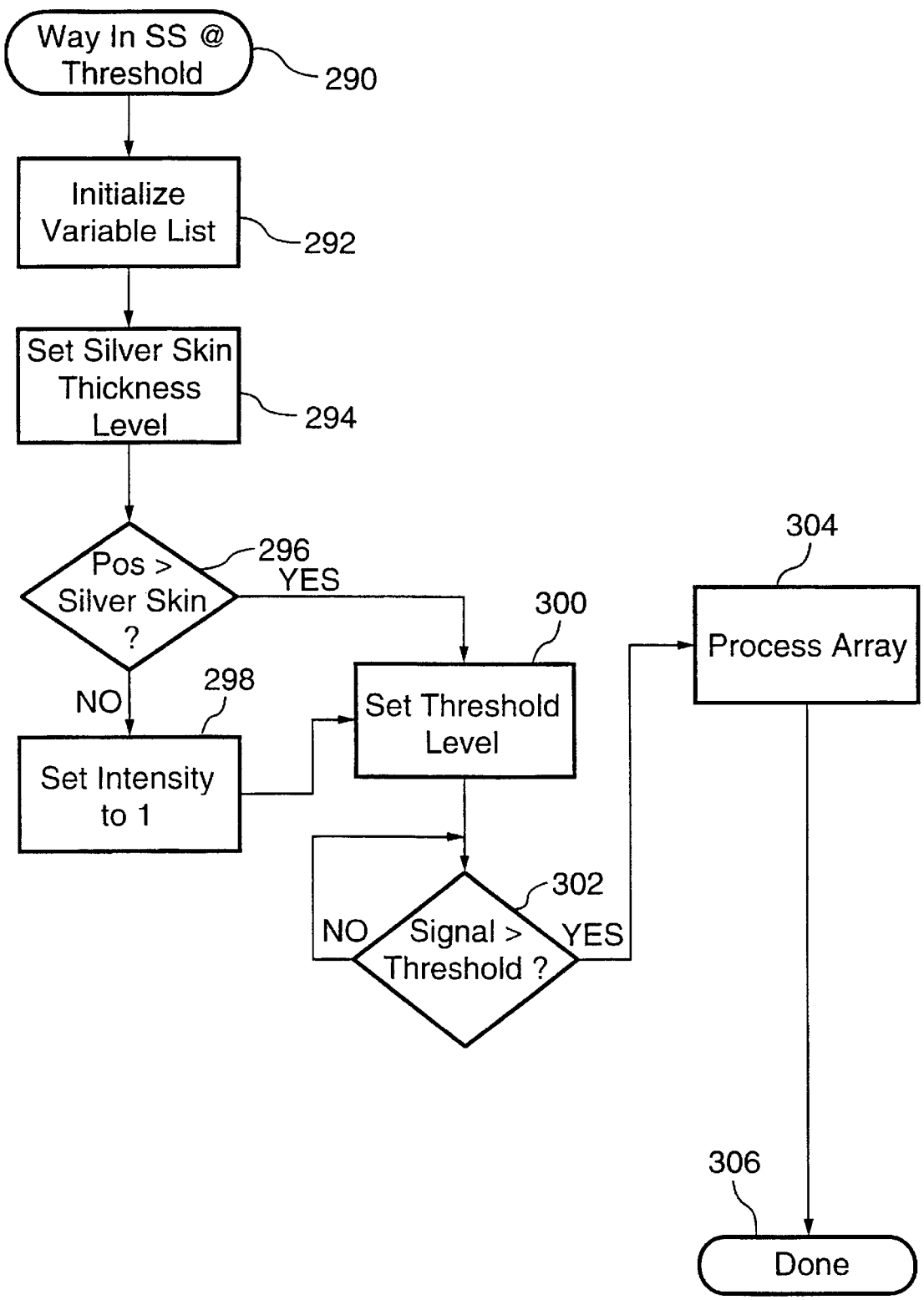
FIG. 12 is a flowchart diagram of the data analysis of fluorescence of silver skin above a threshold level on a penetration pass.

Turning to FIG. 12, the data analysis with respect to fluorescence of silver skin above a threshold level on a penetration pass is described in further detail. At step 290, the processing of the passed raw data array commences. At step 292, the variables for this data set are initialized. These variables are merely a separate instance of the variables as described with respect to FIG. 9 that are particular to this data set. At step 294, the silver skin thickness level position in the meat sample is set as previously discussed. At step 296, the pre-processing of the raw data array is commenced. For each position of penetration on the penetration pass in the data array, the position of penetration is compared with the silver skin thickness position set at step 294. If the position is not greater than the silver skin position, the intensity of fluorescence is set to 1 as indicated at step 298. However, if the position of penetration is greater than the silver skin thickness level position set at step 294, the intensity of fluorescence is not adjusted. The processing then proceeds at step 300. At step 300, the threshold level of fluorescence is set as previously discussed. At step 302, pre-processing of the modified data set is performed. For each point in the modified data set, the signal fluorescence intensity is compared with the threshold level set at step 300. If the signal fluorescence intensity is not greater than the threshold level, then the data point is not analysed and the routine moves on to analyse the next data point. However, if the signal intensity is greater than the threshold level, the data point is added to the data subset array which, along with the variables initialized at step 292 are passed on to be processed as indicated at step 304. The processing of step 304 is described in further detail with respect to FIG. 17. Once the data processing of step 304 is complete, the procedure terminates as indicated at step 306.

Figure 13:
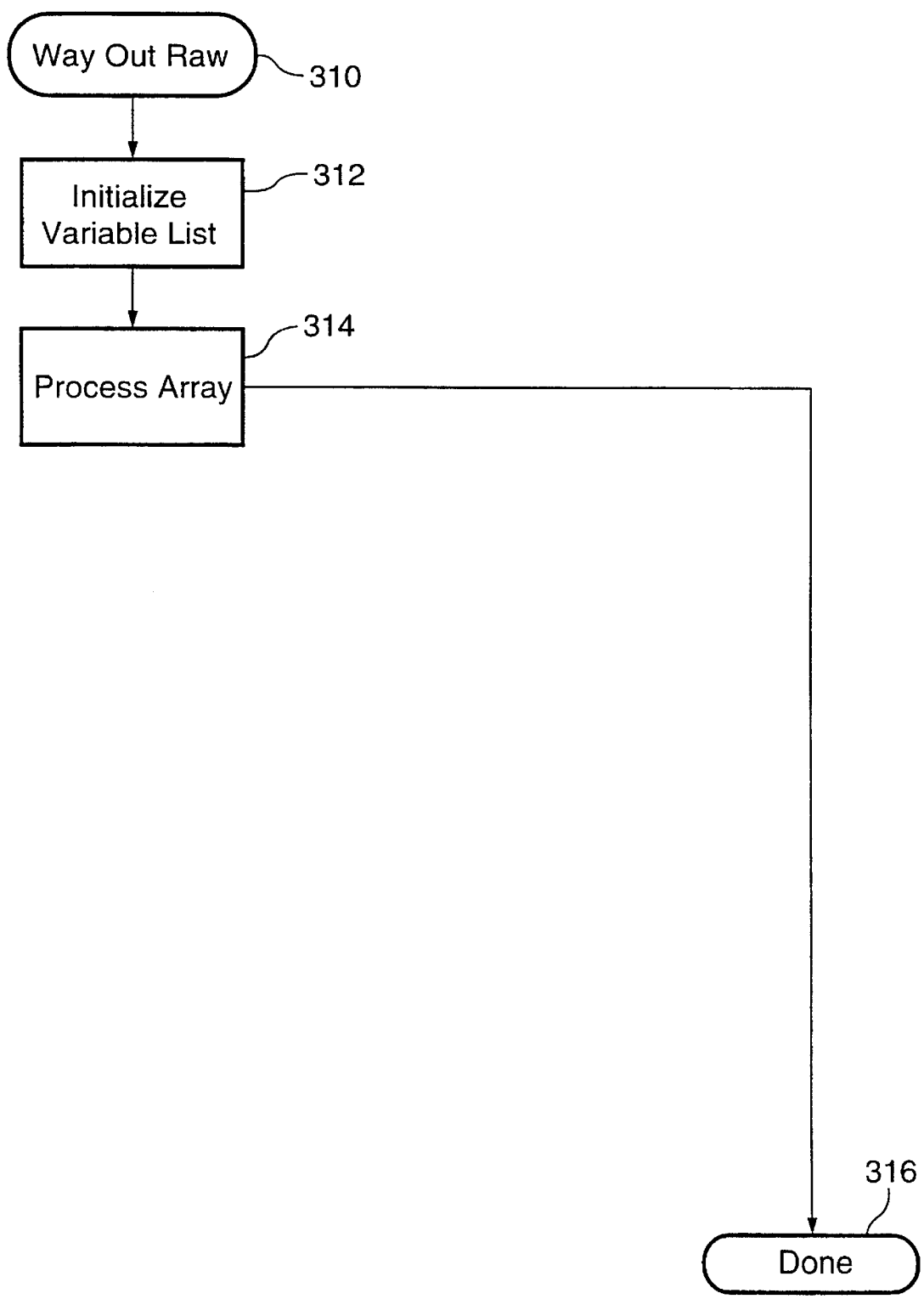
FIG. 13 is a flowchart diagram of the data analysis of raw data regarding fluorescence on a withdrawal pass.

Turning to FIG. 13, the analysis of raw data regarding fluorescence on a withdrawal pass is described in further detail. At step 310, the processing of the data for this data set is commenced by being passed a copy of the raw data array. At step 312, the set of variables with respect to this data set is initialized. These variables are merely a separate instance of the variables as described with respect to FIG. 9 that are particular to this data set. At step 314, the variables from step 312, and a copy of the raw data array is passed to the analysis routine as is further described with respect to FIG. 17. At step 316, the analysis for this data set is complete and the procedure terminates.

Figure 14:
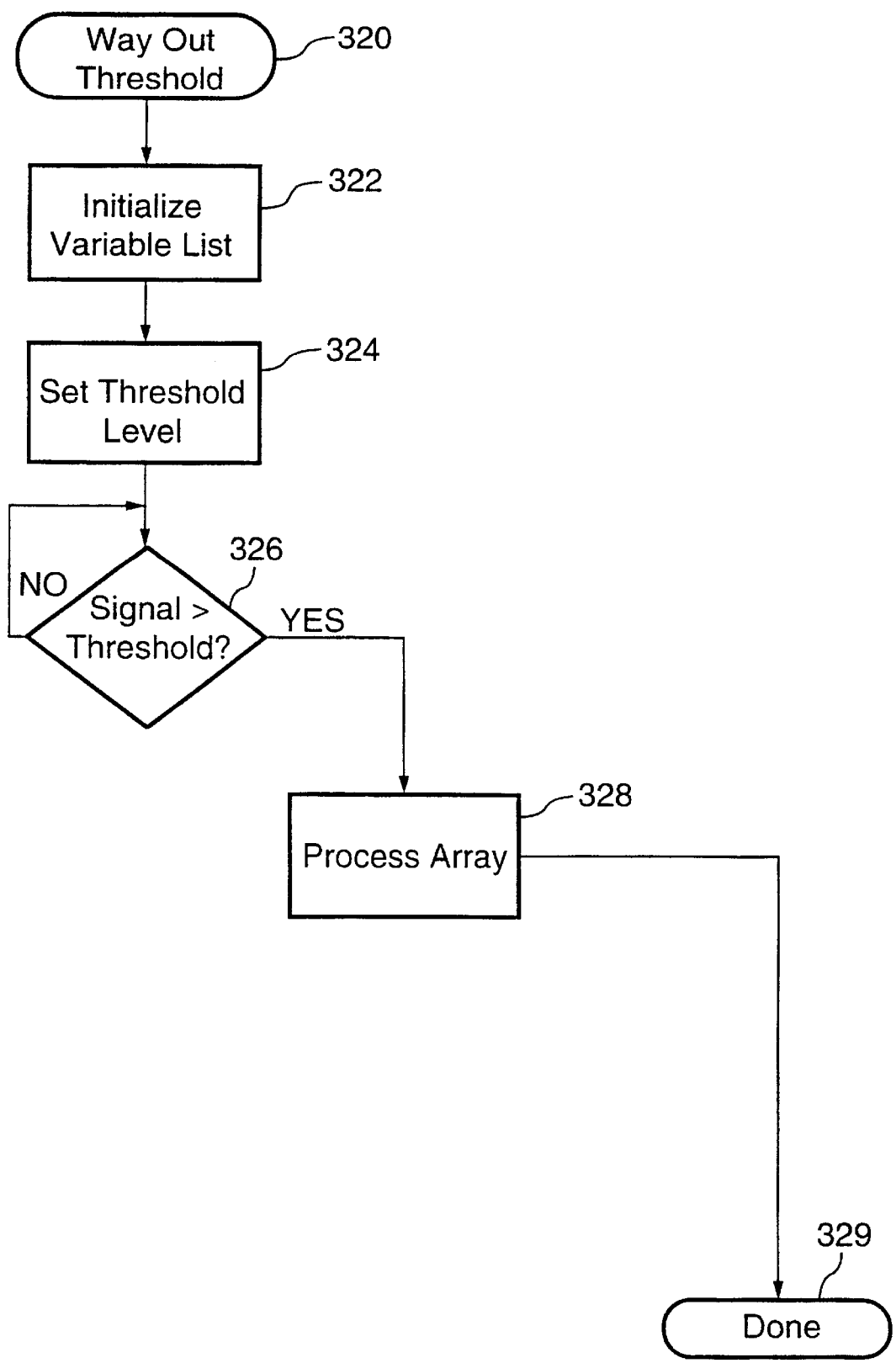
FIG. 14 is a flowchart diagram of the data analysis of fluorescence above a threshold level on a withdrawal pass.

Turning to FIG. 14, the data analysis for fluorescence which is above a threshold level on a withdrawal pass is described in further detail. At step 320, the data analysis for this data set commences by being passed a copy of the raw data array. At step 322, the variables for the data set analysis are initialized. These variables are the same as the variables described with respect to FIG. 9 except that there are instances particular to this data set. At step 324, the threshold level is set as previously discussed.

At step 326, the data is screened to obtain a subset of data which represents values above the threshold level. Each data point in the raw data array on the withdrawal pass is analysed to determine whether the level of fluorescence is above the threshold. The subset of data, in array format meeting the criteria of step 326, as well as the initialized variables at step 322 are passed on to be processed as indicated at step 328. The processing of step 328 is described in further detail with respect to FIG. 17. Once the processing is complete, the procedure terminates as indicated at step 329.

Figure 15:
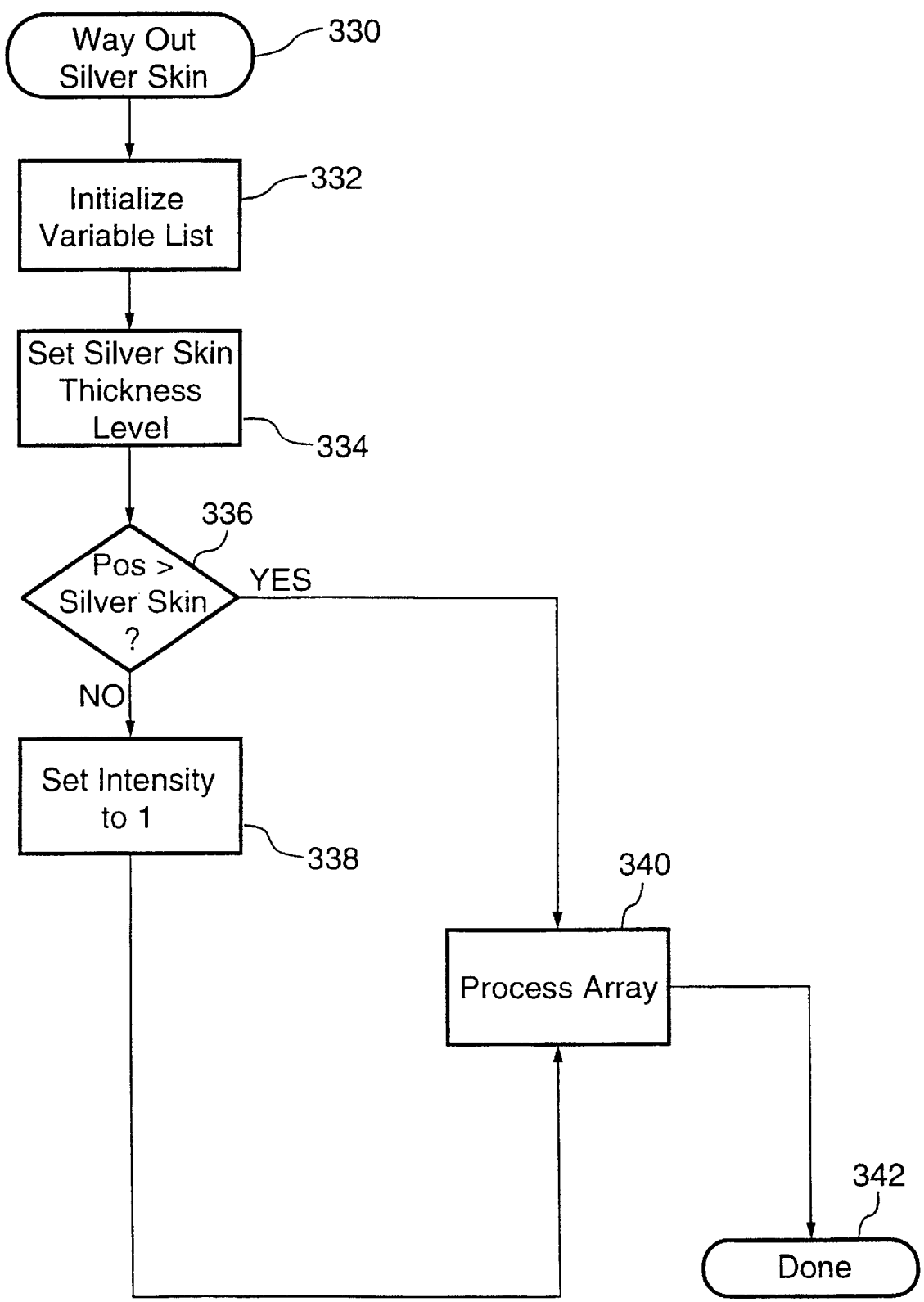
FIG. 15 is a flowchart diagram of the data analysis of fluorescence of silver skin on a withdrawal pass.

Turning the FIG. 15, the data analysis with respect to fluorescence of silver skin on a withdrawal pass is described in further detail. At step 330, the processing for this data set in commenced by being passed a copy of the raw data array. At step 332, the variables for this data set are intialized. These variables are the same as the variables described with respect to FIG. 9 except that there are instances particular to this data set. At step 334, the silver skin thickness level position in the meat sample is set as previously discussed. At step 336, preprocessing of the passed raw data array is provided. For each data point in the array corresponding to the withdrawal pass, the position of the probe is compared with the position of silver skin in the meat sample. If the probe position is not greater than the silver skin position, the level of intensity of fluorescence for that point in the data set is set to 1 as indicated at step 338. The data point is then passed on to be processed as indicated at step 340. However, if the position of penetration for the data point is greater than the silver skin position set at step 334, the level of intensity of fluorescence is not adjusted and the data point is passed on, to be processed at step 340. The variables which were initialized at step 332 as well as the appropriate data points in array format from steps 336 and 338 are passed on to be processed at step 340 as is described in further detail with respect to FIG. 17. Once the data processing is complete for this data set, this procedure terminates as indicated at step 342.

Figure 16:
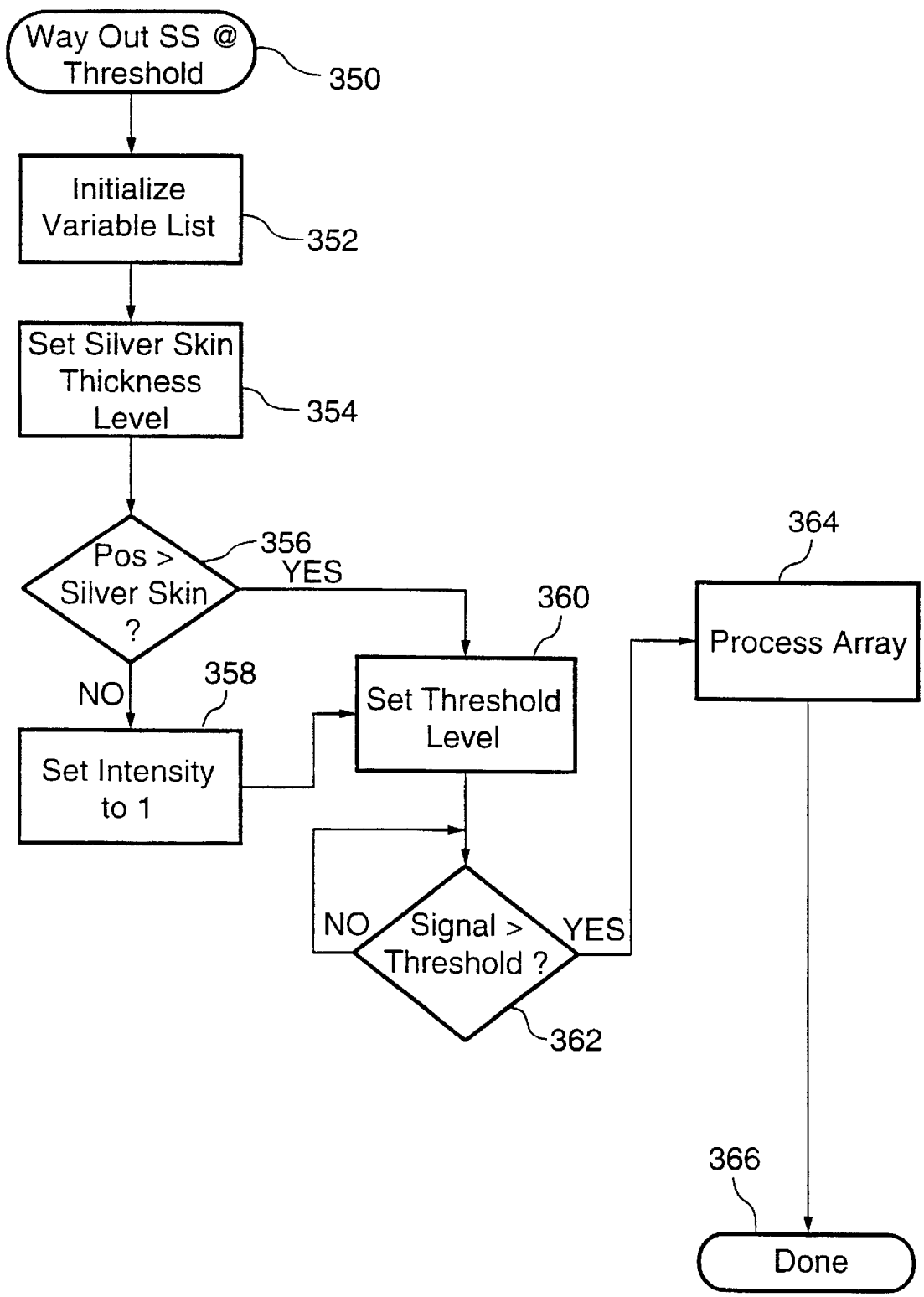
FIG. 16 is a flowchart diagram of the data analysis of fluorescence of silver skin above a threshold level on a withdrawal pass.

Turning to FIG. 16, the data analysis with respect to fluorescence of silver skin above a threshold level on a withdrawal pass is described in further detail. At step 350, the processing of the passed raw data array commences by being passed a copy of the raw data array. At step 352, the variables for this data set are initialized. These variables are merely a separate instance of the variables as described with respect to FIG. 9 that are particular to this data set. At step 354, the silver skin thickness level position in the meat sample is set as previously discussed. At step 356, the pre-processing of the raw data array is commenced. For each position of the probe on the withdrawal pass in the data array, the position of the probe is compared with the silver skin thickness position set at step 354. If the position is not greater than the silver skin position, the intensity of fluorescence is set to 1 as indicated at step 358. However, if the position of the probe is greater than the silver skin thickness level position set at step 354, the intensity of fluorescence is not adjusted. The processing then proceeds at step 360. At step 360, the threshold level of fluorescence is set as previously discussed. At step 362, pre-processing of the modified data set is performed. For each point in the modified data set, the signal fluorescence intensity is compared with the threshold level set at step 360. If the signal fluorescence intensity is not greater than the threshold level, then the data point is not analysed and the routine moves on to analyse the next data point. However, if the signal intensity is greater than the threshold level, the data point is added to the data subset array which, along with the variables initialized at step 352 are passed on to be processed as indicated at step 364. The processing of step 364 is described in further detail with respect to FIG. 17. Once the data processing of step 364 is complete, the procedure terminates as indicated at step 306.

Turning to FIG. 17, the data analysis for peaks and half-peaks is described in further detail. The measurement of half-peak width rather than full peak width simplifies the analysis of fluorescence peaks as a half-peak can be found with relatively few data points. The benefit of measuring half-peaks is that where there is an asymmetry of multiple peaks, the effect is cancelled in the determination of a mean value for half-peak width.

The variables as defined in FIG. 9, are passed to the routine at step 370. As well as a copy of the data set received from any one of the analysis which was described in FIGS. 9 to 16. At step 372, each row of the passed array is compared sequentially starting with the first data element. At step 372, the comparison is made to determine whether any more unprocessed data exists and if not, the procedure terminates at step 398. However, if an additional data points exist, step 374 is executed.

At step 374, the comparison is made between the level of fluorescence at the current position of penetration and if the intensity at the current point is greater, steps 376 to 378 are executed. At step 376, the value flagup is set to true. At step 378, the variable startval is set to the current point of penetration. Moving to step 380, the variable startval is compared to the current position of penetration and if the level of fluorescence has decreased, step 382 is executed. At step 382, the variable flagdown is set to true. However, if at step 380, there has not been a decrease, step 384 is executed wherein the variable flagdown is set to false. At step 386, the comparison is made as to whether both flags, flagup and flagdown, are set to true. If this is the case steps 388 to 396 are executed. At step 388 the peak counter is incremented by 1. At step 390, the flagup variable is set to false. At step 392, the variable peakval is set to a value representing the position of penetration at which the peak occurs. At step 394, the half-peak width is determined by the formula: peakval—startval. At step 396, the total half-peak is incremented by adding the current half-peak width to the sum of the previous half-peak widths. The routine then returns to step 372 to analyse the next data point. Once all of the data points are analysed, the procedure terminates at step 398 and the results and value of variables are passed back to the calling routine.

Figure 18:
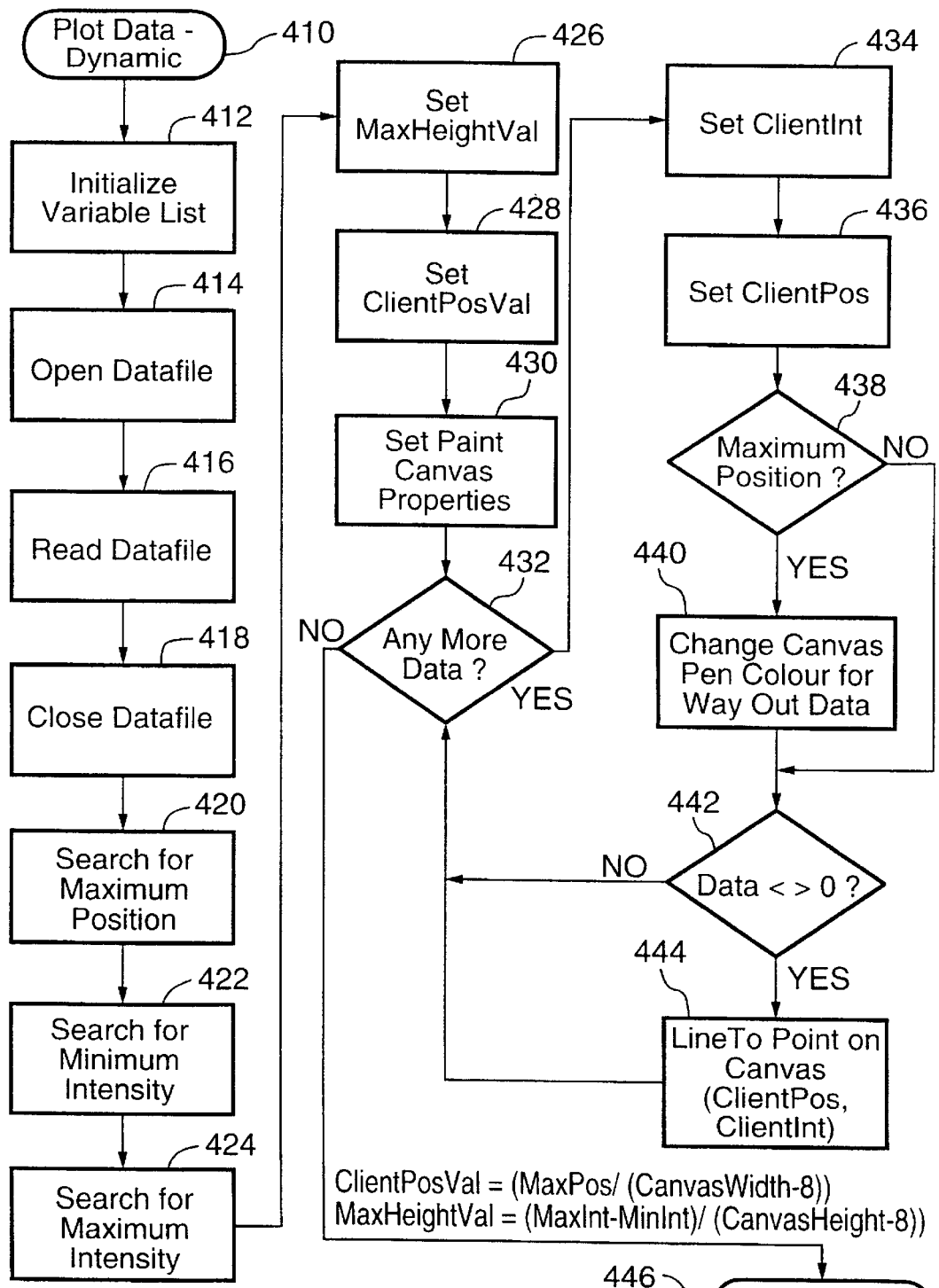
FIG. 18 is a flowchart diagram of the dynamic scaling aspect of the present invention.

The information derived from the raw data set may be analysed and displayed with dynamically scaled axis as described in the flowchart of FIG. 18. There are 9 major variables which are utilized:

| | |
|---|---|
| Maxpos | represents the maximum depth of insertion of the probe; |
| Canvasheight | represents the height of the drawing areas on the screen; |
| Canvaswidth | represents the width of the drawing area on the screen; |
| Minint | represents the minimum intensity of fluorescence recorded on a probe insertion/deletion sequence; |
| Maxint | represents the maximum intensity of fluorescence recorded on a probe insertion/deletion sequence; |
| Maxheightval | represents the dynamically scaled highest point of fluorescence to be displayed on the screen; |
| Clientposval | represents the dynamically scaled further depth point to be displayed on the screen; |
| Clientpos | represents the dynamically scaled depth of the probe at a specific sampling point; and |
| Clientint | represents the dynamically scaled intensity of fluorescence recorded at a specific sampling point on the screen. |

At step 412, the variables clientposval, maxheightval, clientpos, clientint, maxpos, canvaswidth, canvasheight , maxint, and minint are initialized. At step 414, the raw data file containing the carcass number, direction, depth and intensity is opened. At step 416, the values from the raw data file are read into memory in an array-like structure. At step 418, the raw data file is closed. At step 420, the array is searched for the maximum depth recorded, which is stored to the variable maxpos. At step 422, the array is searched for the minimum intensity of fluorescence, the value of which is stored in the variable minint. At step 424, the array is searched for the maximum intensity of fluorescence, and that value is stored in the variable maxint. At step 426, the variable maxheightval is calculated by the formula:

maxheightval=(maxint−minint)÷(canvasheight−8).

At step 428, the variable clientposval is calculated by the formula:

clientposval=[maxpos÷(canvaswidth−8)].

At step 430, the colours to be displayed for the x axis, y axis and other attributes of the display are set. At step 432, the data is in the array, starting at the first element is sequentially processed and displayed on the display device by looping through the array plotting each position on the dynamically scaled axis. For each row of data contained in the array, the test "any more data" results in "yes". At step 434, the variable clientint is set according to the formula:

clientint=canvasheight−(incoming data intensity÷maxheightval)−4.

Utilization of this formula results in the data being dynamically scaled when displayed. At step 436, the variable clientpos is set according to the formula:

clientpos=incoming data [position]÷clientposval.

This formula results in the data being scaled on the x axis. At step 438, a test is performed to determine whether the maximum position of insertion of the probe has been reached. If false, step 442 is executed. If true, step 440 is executed which causes the colour of data on the screen to be changed to represent withdrawal of the probe. At step 442, if the data values are greater than zero, step 444 is executed. At step 444, a line is drawn using the current pen colour from the previous point on the canvas to the position (clientpos, clientint). At step 432, the test is made as to whether all of the data has been processed. If more data exists, the test succeeds and step 434 to 444 are repeated until all of the data has been processed. Once all of the data has been processed, the display of the dynamically scaled data is complete and the data processing routine at step 446 exits.

It is understood that other software approaches may be used to dynamically scale the fluorescent data in order to gather as much information as possible from the collected data in assessing meat tenderness. The embodiment discussed in detail demonstrates the principles of the software which may be used to dynamically scale the data and thereby extract more information from the collected raw data in assessing meat tenderness. It was not until applicants' discovery that additional information could be found in dynamically scaling the collected fluorescent data that one realized that variation in the signal for tender meat was not simply due to noise in the signal, but instead represented further information to assist in meat tenderness evaluation.

DATA ANALYSIS—PREDICTION

The prediction module of as aspect of the present invention may substitute for the visual analysis and operates on the principle of using artificial intelligence techniques to recognize patterns in the fluorescence data obtained from the probe to make a predication of meat tenderness.

An artificial intelligence tool set was chosen for the analysis as it provides a more advanced mechanism for making accurate predictions of meat tenderness. It has been recognized that fluorescent data generated from the probe is not easily characterized for processing using traditional computational methods such as regressional analysis. Advanced artificial intelligence methods are well suited to problems which are tolerant of some imprecision for which a lot of data is available, but where hard and fast rules cannot be easily applied. The present invention utilizes artificial neural network software in the analysis and prediction of meat tenderness.

Artificial neural networks (neural networks) are electronic models which have been created based upon the neural structure of the human brain. Neural networks are particularly useful and well suited to solving problems and recognizing patterns within data and mapping those patterns to pre-set output values. A good description of artificial neural networks has been described in the document "Artificial Neural Network Technology" at the web site "http://www.dacs.dtic.mil/techs/neural". The prediction aspect of the present invention operates on the principle that in choosing salient aspects of the probe data, patterns can be recognized and found by the Neural network software and such patterns can be correlated to meat tenderness. This activity performed by the neural network software operates in a similar manner as a trained technician who views the dynamically scaled data on an output device. Just as the technician utilizes his or her expertise to recognize patterns in the graphical output from the probe, indicative of tenderness, the Neural network software processes the probe data and recognizes within it patterns indicative of meat tenderness.

The use of Neural network software in the present invention employs the principle of supervised learning where the neural network is exposed to feature aspects of fluorescence (the feature variables or signature) for a specific meat sample and the associated level of tenderness which has been previously independently measured for that sample. The neural network processes the signature, by deciding on the appropriate weights to apply to aspects of the signature and then associates the signature features with the desired measure of meat tenderness. A new signature and associated measure of tenderness is then presented to the neural network for processing which the neural network then assimilates into its structure with mistakes or errors made by the neural network in predicting the tenderness value propagated back through the system and weights appropriately adjusted. This process is repeated over and over with a training set of data, validated with a validation set, and the neural network tested with a test set, so that the neural network reaches a point where it is able to reliably predict meat tenderness.

Hence, before prediction can be performed, the neural network software must be taught to recognize patterns by exposing it to a training set, validation set and test set of probe data. The data sets for the training set, validation set and test set are all obtained by using the meat probe on tagged samples of meat and calculating the feature values as previously described with respect to FIGS. 8 to 18. The tagged meat samples are then sent for an independent measure of meat tenderness. Once this independent measure has been taken on each tagged meat sample, these independent measured values are then associated and recorded back with the probe values of fluorescence for each meat sample.

As described with respect to FIGS. 8 to 18, the values for the following variables for each penetration/withdraw pass of the probe in a meat sample is calculated: total half peak width, total number of peaks, number of peaks per unit length, average peak height, average peak width, average half peak unit length and fractional smooth length. These values are determined separately with respect to the penetration pass (way in) and the withdrawal pass (way out) on a probed meat sample, and further calculated with respect to a minimum threshold of fluorescence, and silver skin that may have been encountered on the probing of the meat sample. This yields a vector of 8 different sets of values relating to each penetration/withdraw pass for a sample of meat as outlined in Table 1 below. The values in Table 1 are merely an example of the information collected and calculated on each insertion/withdraw pass of the probe and such values are not meant to limit the scope of the claims.

Tenderness Plan Conference and is more fully described in the document "Standardized Warner-Bratzler Shear Force Procedures for Genetic Evaluation" available at the pages of Texas A&M University at "http:savell-j:tamu.edu/shearstand.html". A prediction for meat tenderness is based upon combining and processing the fluorescent signature of a meat sample on a single insertion/removal pass of the probe to generate a number which corresponds to a predicted Warner-Bratzler shear rating. The Warner-Bratzler shear rating method involves placing a meat sample on a special bench and measuring the force necessary to cut through the meat with a special shear knife. This method yields a number which represents the force, inversely related to tenderness, taken to cut through the meat sample. The drawback to such independent measures of tenderness is that it typically requires the meat to be aged, and cooked, taking a considerable amount of time and effort, before the evaluation can

TABLE 1

| | Way in Raw | Way in Threshold | Way in silver skin | Way in Silver skin threshold | Way out Raw | Way out Threshold | Way out silver skin | Way out silver skin threshold |
|---|---|---|---|---|---|---|---|---|
| Total half peak width | 2 | 9.6923 | 0.1535 | 6.6235 | 563 | 458 | 4 | 480 |
| Total number of peaks | 564 | 2.255 | 47 | 14.7441 | 85 | 80 | 1 | 71 |
| Number of peaks per unit length | 80 | 1.6812 | 3 | 1.1489 | 77 | 5.725 | 4 | 6.7606 |
| Average peak height | 7.05 | 0.7814 | 15.6667 | 0.0234 | 6 | 13.8768 | 0.1735 | 14.6846 |
| Average half peak width | 13.8768 | 488 | | 0.5204 | 77 | 12.8333 | 0.9931 0.6938 | 1.3983 |
| Average half peak per unit length | 1.2229 | 70 | 2.7175 | 6 | 1.0408 | 0.2056 | 0.9931 | 0.0072 |
| fractional smooth length | 0.0217 | 6.9714 | 0.9185 | 12.8333 | 2.2261 | 0.8664 | 5.77 | 0.0234 |

The prediction aspect of the present invention is best illustrated by way of example. Seventy four carcasses between 650–750 pounds from grade A beef were selected within a pH range of 5.4–5.9. The longissimus lumborum (loin) and semimembranosus (inside round) muscles, which differ considerably in fibre type, connective tissue content and fibre orientation were probed using the meat probe at 24 hours post slaughter and data measurements of fluorescence collected from each carcass for later evaluation. Feature variables were calculated for each insertion/withdraw sequence of the probe yielding vectors of values similar to those illustrated in Table 1 and stored for correlation with an independent measure of tenderness.

The carcasses were then set aside for ageing.

Although there are various techniques to evaluating tenderness, such as consumer taste panels, amount of intramuscular fat (marbling), color and surface pH, the Warner-Bratzler shear determination method was preferred and hence used to obtain an independent measure of meat tenderness for purposes of training our selected software. Guidelines for the Warner-Bratzler shear determination method established by a committee of The National Beef be made. While the Warner-Bratzler shear test method was used as an independent measure, it is within the scope of this invention that other independent methods of measuring meat tenderness could be used.

It is well recognized in the literature that tenderness and the perception of tenderness of meat by consumers can vary subject to numerous factors. For example, meat tenderness can depend on such factors as the age of the meat, the cut of the meat, the temperature of the meat, the degree to which the meat has been cooked, among others. For the purposes of illustration of one aspect of the invention, tenderness classes of shear values were chosen as follows:

| | Shear Value (kg) Tenderness Classification | | |
|---|---|---|---|
| Muscle | High | Medium | Low |
| Semimembranous | <5.76 | 5.77–8.14 | >8.14 |
| Longissimus lumborum | <5.55 | 5.56–7.83 | >7.83 |

It should be understood that the values for the tenderness classifications are subject to variation and adjustment set out above depending on both objective and subjective factors of tenderness. For example, individuals of a different social upbringing, or from a different geographical region, not having been exposed to "tender" meat, might judge a "tough" piece of meat as being tender in a subjective consumer taste test. In addition, for example, different cuts of meat may also be classified with different values for high, medium or low levels of tenderness depending upon the circumstances and the choice of classification measures chosen by the individual practicing the invention. Therefore, probed meat samples can be immediately categorized regarding tenderness as low, medium and high from the predicted Warner-Bratzler shear ratings obtained from probe measurements. This is immediately useful as it allows the farmer, meat packer, butcher and consumer to reliably know the character of the meat sample and deal with it accordingly. The grading of meat into tenderness classifications has the additional benefit of providing a result that is easily understood as compared to the Warner-Bratzler shear rating number.

After seven days of ageing, muscle samples were cut from the carcasses for the Warner-Bratzler shear determinations on cooked fresh muscle. The meat was broiled to an internal temperature of 72° C. Three 19 millimeter cores were cut from the steaks for the shear analysis. Cores taken parallel to the muscles grain were sheared perpendicular to the muscle grain on an Instron 4201 device equipped with a Warner-Bratzler head and the results averaged.

The shear values from the longissimus lumborun muscles obtained from the 74 meat samples is illustrated in Table 2 below. The minimum shear value of the set of 74 meat samples was approximately 4, the maximum approximately 13.3, with the mean at 7.1 and most shear values falling between 5.2 and 8.7.

TABLE 2

| Warner-Bratzler Measured Shear Value Range | Frequency |
| --- | --- |
| 4.003 | 1 |
| 5.16775 | 10 |
| 6.3325 | 20 |
| 7.49725 | 16 |
| 8.662 | 15 |
| 9.82675 | 4 |
| 10.9915 | 3 |
| 12.15625 | 3 |
| 13.3 | 2 |

As shown in Table 2, there was one sample with a measured shear value of 4.003. There were 10 samples with measured shear values between 4.003 and 5.16775, and so on.

The Warner-Bratzler shear rating value for each sample of meat was then associated as the desired output value with the fluorescent signature of each respective meat sample.

The data from the probe using the feature variables computed as described above at 24 hours post slaughter was compared with the Warner-Bratzler shear readings at 7 seven days post slaughter to train the neural network.

To obtain a valuable predictor of meat tenderness, it has been determined that the data sets relating to "way in" silver skin, "way in" threshold, "way out" silver skin and "way out" threshold are particularly useful. By utilizing the feature variables of total half peak width, total number of peaks, number of peaks per unit length, average half peak height, average half peak width, average half peak width per unit length and fractional smooth length for "way in" silver skin, "way in" threshold, "way out" silver skin and "way out" threshold, this example has shown that a reliable prediction of meat tenderness can be obtained from the fluorescent signature of the tested section of meat.

The feature variables calculated from the data from the probe, and the Warner-Bratzler shear test data were analysed using Predict Version 2.0 from NeuralWare, release 3.0 which is a back propagation network. A 3-layer model of 25:3:1 (ratios of input: to hidden: to output layer neurons) was used, with learning ratio of 0.1, initial weight of 0.3, input variables mapped to a (−1, 1) range and learning based on a logistic activation function. All standard defaults were used, except for noise level, which was set to a level which accommodates considerable signal noise. The analysis was done using a round robin procedure. The round robin procedure was chosen as it is less likely to generate a "fluke" high $R^2$ value. The round robin procedure involves a data training, testing and validation process. The $R^2$ values represent a measure of how closely related the variables calculated from the data on fluorescence gathered from the probe are to the connective tissue as predicted by the Warner-Bratzler shear test.

From the data from the 74 meat samples, a training set of 60 samples was used to train the neural network, a set of 7 samples was used to test the network, and a set of 7 samples was used in the validation/production set. After the network was trained, the production set was applied to the trained net software to calculate the effectiveness of the network. Hence, the production $R^2$ is the $R^2$ when a trained net is applied to a data set that the net has never seen before. The results of the correlation are illustrated in Table 3 below. The number of inputs was set to 25, resulting in a network structure is of 9–3–1 with $R^2$=0.64. for the 7 validation cases.

TABLE 3

| seed #2 | | 10% validn/10% test sets selected by round robin default settings except noise level set to noisy | | | | | reduced to 25 inputs dropped grps 2, 3, 6, 7 Accuracy (Conf. Inter Records) | | |
| --- | --- | --- | --- | --- | --- | --- | --- | --- | --- |
| 9-3-1 | shr_3 | R | Net-R | Avg.Abs. | Max.Abs | RMS | | | |
| | All | 0.709088 | 0.691637 | 1.101887 | 5.009863 | 1.456426 | 0.837838 | 2.887931 | 74 |
| | Train | 0.717574 | 0.701177 | 1.098891 | 5.009863 | 1.448414 | 0.85 | 2.885471 | 60 |
| | Test | 0.947509 | 0.917817 | 1.104166 | 2.058321 | 1.33673 | 0.714286 | 3.272307 | 7 |
| $R^2$ = 0.639824 | Valid | 0.79989 | 0.798687 | 1.125286 | 3.865207 | 1.62941 | 0.857143 | 3.988785 | 7 |

In the above data, the probe explains or predicts 64% of the variation of tenderness measured by the Warner-Bratzler shear test.

The values predicted by the neural network software, and the actual measured shear values, for the production set are shown in Table 4 below.

TABLE 4

| Neural Network Predicted Shear Value | Warner-Bratzler Measured Shear Value | Tenderness Category |
|---|---|---|
| 6.188 | 7.563 | medium |
| 7.027 | 10.892 | medium |
| 5.106 | 4.591 | high |
| 6.590 | 6.042 | medium |
| 5.614 | 5.429 | high |
| 6.227 | 6.613 | medium |
| 7.454 | 8.457 | medium |

With the neural net developed and validated according to the procedure above, an accurate prediction of meat tenderness can be made.

It is recognized that the number of cases used to train and test the neural network can improve the accuracy of the prediction. By increasing the number of cases, and adjusting the parameters of the neural network software used, it should be possible to improve on the accuracy of the prediction of meat tenderness.

Various aspects of the invention have been described in detail. It is appreciated that variations may be made thereto without departing from the spirit of the invention or scope of the appended claims.

I claim:

1. A method for predicting meat quality of a meat sample by analyzing data representative of a fluorescent signal generated by a meat probe inserted in and withdrawn from said meat sample; said data being in two sets, a first set representative of said fluorescent signal generated by said probe on "way in" during probe insertion and a second set representative of said fluorescent signal generated by said probe on "way out" during probe withdrawal; said method comprising:

i) analyzing said data by use of a trained artificial neural network structure where said analysis is carried out on selected said first set of data, said second set of data or both said first and second sets of data;

ii) developing by way of said trained artificial neural network structure analyzing said selected data, a value representative of level of meat quality; and iii) classifying level of meat quality of said meat sample according to said value.

2. A method of claim 1 wherein said data of said first or second set is input into said trained artificial neural network structure as feature variables selected from the group consisting of:

total half peak width;
   average half peak width per unit length;
   total number of peaks;
   number of peaks per unit length;
   average peak height;
   half peak width;
   fractional smooth length;
   total peak width (all peaks); and
   average half peak width.

3. A method of claim 2, wherein said selected feature variables comprise:

total half peak width;
   average half peak width per unit length; and
   at least one remaining feature variable selected from said group.

4. A method of claim 3 wherein said selected feature variables comprise:

total half peak width;
   average half peak width per unit length;
   total number of peaks; and
   fractional smooth length.

5. A method of claim 4 wherein said selected feature variables comprise:

total half peak width;
   average half peak width per unit length;
   total number of peaks;
   fractional smooth length;
   number of peaks per unit length;
   average peak height; and
   half peak width.

6. A method of claim 5 wherein said data is derived from correlating signal intensity with depth of penetration of said probe in said sample, said fluorescent signal being a series of spaced-apart peaks and valleys for either "way in" or "way out" pass of said probe.

7. A method of claim 6 wherein said correlation determines fluorescent intensity value at an interval in said signal which is representative of a unit of penetration in said sample.

8. A method of claim 5 wherein said fluorescent signal is an analog signal, converting amplitude of said analog signal into a digital signal representative of amplitude, sampling said digital signal at intervals representative of depth of penetration in a meat sample.

9. A method of claim 8 wherein said analog fluorescent signal is transmitted along a plastic optic fibre from said probe to a data processor, said plastic optic fibre being capable of transmitting said signal with a signal to noise ratio in excess of 100 to 1.

10. A method of claim 1 wherein said classified level of meat quality is correlated with said meat sample.

11. A method of claim 10 wherein said meat sample is a carcass, correlating said classified level of meat quality with said carcass.

12. A method of claim 10 wherein said level of meat quality is a measure of degree of meat tenderness.

13. A method of claim 12 wherein said degree of meat tenderness is classified as low, medium or high.

14. A method of claim 1 wherein said meat quality classification is developed by correlating an analyzed pattern of said data to a pattern representative of a level of meat quality.

15. A method of claim 14 wherein said trained artificial neural network structure has been taught three patterns representative of low, medium, and high meat tenderness which is correlated with corresponding levels of meat quality.

16. A method of training artificial intelligence software to predict tenderness of a meat sample from a signal representative of fluorescence generated by a meat probe comprising:

i) calculating one or more fluorescent feature variables of:
      total half peak width;
      average half peak width per unit length;

total number of peaks;
fractional smooth length;
number of peaks per unit length;
average peak height;
half peak width;
total peak width (all peaks) and
average half peak width;

ii) independently obtaining a measure of meat tenderness of said meat sample;

iii) inputting said feature variables into artificial intelligence software;

iv) inputting said measure of meat tenderness into said artificial intelligence software;

v) teaching said artificial intelligence software to recognize patterns within said feature variables and associate said patterns with said measure of tenderness;

vi) repeating steps i) to v) above until said artificial intelligence software is able to correlate said values with said measure of meat tenderness to a value at least greater than 6.

17. A method of claim 16 wherein said meat samples are classified as having low, medium and high degrees of tenderness to teach said software to develop three distinct patterns corresponding to said three distinct degrees of tenderness.

18. A method of claim 16, wherein said calculated feature variables are
   total half peak width;
   average half peak width per unit length; and
   at least one remaining feature variable selected from said group.

19. A method of claim 18 wherein said calculated feature variables are:
   total half peak width;
   average half peak width per unit length;
   total number of peaks; and
   fractional smooth length.

20. A method of claim 19 wherein said calculated feature variables are:
   total half peak width;
   average half peak width per unit length;
   total number of peaks;
   fractional smooth length;
   number of peaks per unit length;
   average peak height; and
   half peak width.

21. A method of training neural network software to predict meat tenderness from a signal representative of fluorescence using the components of the signal of:
   total half peak width;
   average half peak width per unit length; and
   at least one feature variable selected from the group consisting of:
     total number of peaks number of peaks;
     fractional smooth length;
     number of peaks per unit length;
     average peak height; and
     half peak width.

* * * * *